(12) United States Patent
Seward

(10) Patent No.: US 10,842,969 B2
(45) Date of Patent: Nov. 24, 2020

(54) SYSTEMS AND METHODS OF TREATING MALACIA BY LOCAL DELIVERY OF HYDROGEL TO AUGMENT TISSUE

(71) Applicant: MERCATOR MEDSYSTEMS, INC., Emeryville, CA (US)

(72) Inventor: Kirk Patrick Seward, San Francisco, CA (US)

(73) Assignee: MERCATOR MEDSYSTEMS, INC., Emeryville, CA (US)

( * ) Notice: Subject to any disclaimer, the term of this patent is extended or adjusted under 35 U.S.C. 154(b) by 0 days.

(21) Appl. No.: 15/142,794

(22) Filed: Apr. 29, 2016

(65) Prior Publication Data

US 2016/0243333 A1  Aug. 25, 2016

Related U.S. Application Data

(63) Continuation-in-part of application No. 14/522,984, filed on Oct. 24, 2014.
(Continued)

(51) Int. Cl.
*A61L 29/08* (2006.01)
*A61L 29/16* (2006.01)
(Continued)

(52) U.S. Cl.
CPC ....... *A61M 25/0084* (2013.01); *A61K 31/337* (2013.01); *A61L 27/52* (2013.01);
(Continued)

(58) Field of Classification Search
CPC .......... A61M 25/0084; A61M 25/1029; A61M 25/003; A61M 2025/1059;
(Continued)

(56) References Cited

U.S. PATENT DOCUMENTS 6,129,739 A    10/2000   Khosravi
6,152,943 A    11/2000   Sawhney
(Continued)

FOREIGN PATENT DOCUMENTS

CN    101573108 A    11/2009
JP    2007502690 A    2/2007
(Continued)

OTHER PUBLICATIONS

Braun Interventional Systems, Inc. Percutaneous Transluminal Sizing Balloon Catheter. Brochure, Jan. 2011.*
(Continued)

*Primary Examiner* — Dinah Baria
(74) *Attorney, Agent, or Firm* — Wilson Sonsini Goodrich & Rosati

(57) ABSTRACT

Systems, devices, and methods for maintaining patency in a bronchus of a patient are presented. A catheter is positioned within the bronchus. A target region of one or more of a bronchial wall, submucosa, media, and adventitia is punctured with an injection needle disposed on a distal end of the catheter. Such puncturing is achieved by expanding a balloon disposed on the distal end of the catheter. The balloon may be comprised of at least two materials of different elastic modulus, which allows for a flexible but relatively non-distensible, unfolding component of the balloon as well as an elastomeric, inflatable component of the balloon. Through the injection needle, an amount of one or more crosslinking agents is delivered to the target region. The delivered amount is effective to provide structural support for the bronchial wall, substituting for the bronchial cartilage thereby treating bronchomalacia.

20 Claims, 15 Drawing Sheets

Related U.S. Application Data

(60) Provisional application No. 61/895,779, filed on Oct. 25, 2013, provisional application No. 62/155,172, filed on Apr. 30, 2015.

(51) Int. Cl.

| | | |
|---|---|---|
| *A61F 2/04* | (2013.01) | |
| *A61M 25/00* | (2006.01) | |
| *A61M 25/10* | (2013.01) | |
| *A61K 31/337* | (2006.01) | |
| *A61L 29/14* | (2006.01) | |
| *A61L 27/52* | (2006.01) | |
| *A61M 25/01* | (2006.01) | |
| *A61N 1/05* | (2006.01) | |
| *A61B 5/00* | (2006.01) | |

(52) U.S. Cl.
CPC ........... *A61L 29/14* (2013.01); *A61M 25/003* (2013.01); *A61M 25/10* (2013.01); *A61M 25/1029* (2013.01); *A61B 5/489* (2013.01); *A61B 5/6852* (2013.01); *A61L 2300/416* (2013.01); *A61M 25/0108* (2013.01); *A61M 2025/0087* (2013.01); *A61M 2025/0092* (2013.01); *A61M 2025/0093* (2013.01); *A61M 2025/0183* (2013.01); *A61M 2025/105* (2013.01); *A61M 2025/1059* (2013.01); *A61M 2025/1086* (2013.01); *A61M 2210/1032* (2013.01); *A61M 2210/1035* (2013.01); *A61N 1/0529* (2013.01)

(58) Field of Classification Search
CPC .. A61M 2025/0183; A61M 2025/0087; A61M 25/0108; A61M 25/01032; A61L 27/52; A61L 29/14; A61K 31/337; A61N 1/0529; A61F 2002/043; A61F 2002/046; A61F 2002/04; A61F 2002/82
See application file for complete search history.

(56) References Cited

U.S. PATENT DOCUMENTS

| | | |
|---|---|---|
| 6,165,201 A | 12/2000 | Sawhney et al. |
| 6,179,861 B1 | 1/2001 | Khosravi et al. |
| 6,179,862 B1 | 1/2001 | Sawhney |
| 6,203,561 B1 | 3/2001 | Ramee et al. |
| 6,214,026 B1 | 4/2001 | Lepak et al. |
| 6,221,091 B1 | 4/2001 | Khosravi |
| 6,371,970 B1 | 4/2002 | Khosravi et al. |
| 6,514,534 B1 | 2/2003 | Sawhney |
| 6,530,939 B1 | 3/2003 | Hopkins et al. |
| 6,544,279 B1 | 4/2003 | Hopkins et al. |
| 6,566,406 B1 | 5/2003 | Pathak et al. |
| 6,589,263 B1 | 7/2003 | Hopkins et al. |
| 6,605,294 B2 | 8/2003 | Sawhney |
| 6,610,033 B1 | 8/2003 | Melanson et al. |
| 6,616,679 B1 | 9/2003 | Khosravi et al. |
| 6,620,182 B1 | 9/2003 | Khosravi et al. |
| 6,632,457 B1 | 10/2003 | Sawhney |
| 6,663,651 B2 | 12/2003 | Krolik et al. |
| 6,673,093 B1 | 1/2004 | Sawhney |
| 6,689,148 B2 | 2/2004 | Sawhney et al. |
| 6,703,047 B2 | 3/2004 | Sawhney et al. |
| 6,818,018 B1 | 11/2004 | Sawhney |
| 6,860,867 B2 | 3/2005 | Seward et al. |
| 6,887,257 B2 | 5/2005 | Salahieh et al. |
| 6,887,974 B2 | 5/2005 | Pathak |
| 7,009,034 B2 | 3/2006 | Pathak et al. |
| 7,025,990 B2 | 4/2006 | Sawhney |
| 7,057,019 B2 | 6/2006 | Pathak |
| 7,141,041 B2 | 11/2006 | Seward |
| 7,211,651 B2 | 5/2007 | Pathak |
| 7,220,270 B2 | 5/2007 | Sawhney et al. |
| 7,306,618 B2 | 12/2007 | Demond et al. |
| 7,332,566 B2 | 2/2008 | Pathak et al. |
| 7,347,850 B2 | 3/2008 | Sawhney |
| 7,410,491 B2 | 8/2008 | Hopkins et al. |
| 7,413,752 B2 | 8/2008 | Sawhney |
| 7,582,111 B2 | 9/2009 | Krolik et al. |
| 7,592,418 B2 | 9/2009 | Pathak et al. |
| 7,597,882 B2 | 10/2009 | Pathak et al. |
| 7,605,232 B2 | 10/2009 | Pathak |
| 7,648,518 B2 | 1/2010 | Salahieh et al. |
| 7,648,713 B2 | 1/2010 | Sawhney |
| 7,744,584 B2 | 6/2010 | Seward et al. |
| 7,744,913 B2 | 6/2010 | Noyes |
| 7,776,063 B2 | 8/2010 | Sawhney et al. |
| 7,780,980 B2 | 8/2010 | Sawhney |
| 7,862,538 B2 | 1/2011 | Sawhney et al. |
| 7,862,601 B2 | 1/2011 | Sanati et al. |
| 7,872,068 B2 | 1/2011 | Khosravi et al. |
| 7,914,541 B2 | 3/2011 | Sawhney et al. |
| 7,981,134 B2 | 7/2011 | Salahieh et al. |
| 7,993,363 B2 | 8/2011 | Demond et al. |
| 8,003,705 B2 | 8/2011 | Sawhney et al. |
| 8,044,137 B2 | 10/2011 | Khosravi et al. |
| 8,052,713 B2 | 11/2011 | Khosravi et al. |
| 8,105,622 B2 | 1/2012 | Sawhney |
| 8,123,777 B2 | 2/2012 | Krolik et al. |
| 8,257,723 B2 | 9/2012 | Noyes |
| 8,267,956 B2 | 9/2012 | Salahieh et al. |
| RE43,882 E | 12/2012 | Hopkins et al. |
| RE43,902 E | 1/2013 | Hopkins et al. |
| 8,383,161 B2 | 2/2013 | Campbell et al. |
| 8,409,606 B2 | 4/2013 | Sawhney et al. |
| 8,460,336 B2 | 6/2013 | Krolik et al. |
| 8,486,105 B2 | 7/2013 | Demond et al. |
| 8,512,749 B2 | 8/2013 | Sawhney et al. |
| 8,535,705 B2 | 9/2013 | Pathak et al. |
| 8,557,535 B2 | 10/2013 | Pathak |
| 8,562,639 B2 | 10/2013 | Khosravi et al. |
| 8,563,027 B2 | 10/2013 | Jarrett et al. |
| 8,617,201 B2 | 12/2013 | Hopkins et al. |
| 8,702,777 B2 | 4/2014 | Krolik et al. |
| 8,708,995 B2 | 4/2014 | Seward et al. |
| 8,795,709 B2 | 8/2014 | Sawhney et al. |
| 8,852,230 B2 | 10/2014 | Sawhney et al. |
| 8,852,646 B2 | 10/2014 | Campbell et al. |
| 8,911,232 B2 | 12/2014 | Nguyen et al. |
| 8,961,501 B2 | 2/2015 | Jarrett et al. |
| 8,986,730 B2 | 3/2015 | Sawhney et al. |
| 9,061,098 B2 | 6/2015 | Seward et al. |
| 2002/0188310 A1 | 12/2002 | Seward et al. |
| 2003/0005546 A1 | 1/2003 | Bone |
| 2003/0055400 A1 | 3/2003 | Seward et al. |
| 2003/0171734 A1 | 9/2003 | Seward et al. |
| 2004/0101518 A1 | 5/2004 | Vacanti et al. |
| 2004/0121965 A1 | 6/2004 | Greenberger et al. |
| 2004/0188203 A1 | 9/2004 | Gold et al. |
| 2005/0042295 A1* | 2/2005 | Hunter ................... A61K 45/06 424/486 |
| 2005/0043752 A1* | 2/2005 | Phan ..................... A61B 17/064 606/155 |
| 2005/0137611 A1 | 6/2005 | Escudero et al. |
| 2006/0025815 A1* | 2/2006 | McGurk ........... A61B 17/00491 606/213 |
| 2006/0263434 A1 | 11/2006 | Desai et al. |
| 2007/0282366 A1* | 12/2007 | Khosravi ............... A61L 24/046 606/192 |
| 2008/0004596 A1* | 1/2008 | Yun ................... A61M 25/0084 604/508 |
| 2008/0009683 A1* | 1/2008 | Bogoni ................. A61B 5/085 600/300 |
| 2008/0171978 A1 | 7/2008 | Quigley |
| 2008/0249503 A1 | 10/2008 | Fields et al. |
| 2008/0276935 A1 | 11/2008 | Wang |
| 2008/0300571 A1 | 12/2008 | Lepivert |
| 2009/0082295 A1 | 3/2009 | Jungnelius et al. |
| 2010/0145307 A1 | 6/2010 | Seward et al. |
| 2010/0202979 A1 | 8/2010 | Horn |
| 2011/0294952 A1 | 12/2011 | Petersen |

(56) References Cited

U.S. PATENT DOCUMENTS

| | | | |
|---|---|---|---|
| 2012/0231047 A1* | 9/2012 | Herrmann | A61P 11/06 424/400 |
| 2012/0259216 A1 | 10/2012 | Gerrans et al. | |
| 2013/0116341 A1 | 5/2013 | Askari et al. | |
| 2013/0237909 A1 | 9/2013 | Orr | |
| 2013/0267996 A1* | 10/2013 | Sawhney | A61B 17/00491 606/214 |
| 2015/0119850 A1 | 4/2015 | Kirk | |

FOREIGN PATENT DOCUMENTS

| | | |
|---|---|---|
| WO | WO-9503036 A1 | 2/1995 |
| WO | WO-2006089290 A1 | 8/2006 |
| WO | WO-2008013747 A2 | 1/2008 |
| WO | WO-2015061748 A9 | 4/2015 |

OTHER PUBLICATIONS

International Application No. PCT/US2014/062273 Preliminary Report on Patentability dated Apr. 26, 2016.

International search report and written opinion dated Feb. 4, 2015 for PCT/US2014/062273.

International Application No. PCT/US2016/030009 International Search Report and Written Opinion dated Jul. 26, 2016.

U.S. Appl. No. 14/522,984 Final Office Action dated Jul. 27, 2017.

U.S. Appl. No. 14/522,984 Office Action dated Jan. 25, 2017.

International Application No. PCT/US2016/030009 International Preliminary Report on Patentability dated Nov. 9, 2017.

U.S. Appl. No. 14/522,984 Non-Final Office Action dated Mar. 22, 2018.

U.S. Appl. No. 14/522,984 Final Office Action dated Nov. 29, 2018.

U.S. Appl. No. 14/522,984 Non-Final Office Action dated Mar. 29, 2019.

Al-Ghananeem et al.: Intratumoral Delivery of Paclitaxel in Solid Tumor from Biodegradnable Hyaluronan Nanoparticle Formulations. AAPS PharmSciTech 10(2): 410-417 (2009).

Celikoglu et al.: Intratumoral Administration of Cisplatin Through a Bronchoscope Followed by Irradiation for Treatment of Inoperable Non-Small Cell Obstructive Lung Cancer. Lung Cancer 51: 225-236 (2006).

Celikoglu et al.: Bronchoscopic Intratumoral Chemotherapy of Lung Cancer. Lung Cancer 61: 1-12 (2008).

European Patent Application No. 14856589.8 Extended European Search Report dated May 22, 2017.

Tsukada et al.: Macro and Microscopic Evaluation of Paclitaxel Delivery in the Airway with a Novel Endobronchial Injectable Drug Delivery Catheter. European Respiratory Journal 42(57): P3760 (2013).

U.S. Appl. No. 14/522,984 Final Office Action dated Nov. 4, 2019.

\* cited by examiner

SYSTEMS AND METHODS OF TREATING MALACIA BY LOCAL DELIVERY OF HYDROGEL TO AUGMENT TISSUE

CROSS-REFERENCE

This application is a continuation-in-part of U.S. patent application Ser. No. 14/522,984, filed Oct. 24, 2014, which claims the benefit of U.S. Provisional Application No. 61/895,779, filed Oct. 25, 2013, and also claims priority to U.S. Provisional Application No. 62/155,172, filed Apr. 30, 2015, which applications are incorporated herein by reference.

BACKGROUND OF THE INVENTION

The present invention relates generally to medical methods and devices. More particularly, the present invention relates to intraluminal catheters with balloons having segments with different material moduli, which upon inflation improve apposition of tools against luminal structures, such as blood vessel walls or walls of other body lumens such as bronchi or the urethra. The present invention further relates to methods and systems for delivering agents adjacent to or within the encircling or encapsulating smooth muscle or connective tissue component of a conduit, vessel, or cavitary organ for the prophylaxis or treatment of disease.

Of particular interest to the present invention is the treatment of bronchial diseases. The bronchi in the respiratory tract conduct air into the lungs. Smooth muscle is present continuously around the bronchi. Many diseases of or around bronchial passageways can cause obstruction or narrowing of the bronchi. Cancer can be such a cause of narrowing for which medication delivered directly into the wall, whether anti-inflammatory, chemotherapeutic, paralytic, or otherwise may reduce the luminal narrowing and improve airflow without constriction.

Current estimates show that 226,000 people will be diagnosed in 2012 with lung and bronchial carcinoma in the U.S. About 160,000 of them are expected to die from this disease or its complications, such as obstructed airways. This disease impacts males and females with median age at death of 72 years. Malignant airway obstruction may potentially be treated with local, direct infusion of therapeutic agents into the bronchial wall and adventitia (the tissue between smooth muscle layers and cartilage) or directly into the tumor. Also, many other diseases of the bronchi, such as malignant airway obstruction, asthma, chronic bronchitis, arise in the sub-epithelial bronchial wall, and thus local treatment beyond the epithelium may be warranted.

In addition, other diseases of the airway may benefit from localized delivery of medication, fluids, bulking agents, biotherapeutics, or diagnostics. For example, tracheobronchial malacia or excessive dynamic airway collapse may be treated with bulking or sclerosing agents to stiffen the airway wall and prevent expirational collapse of the airway. Mucous hypersecretion may be treated with agents to reduce the production of mucous, whether by killing or by altering mucous producing cells. Obstructive pulmonary diseases such as asthma or other non-cancerous obstructive disease may be caused by extensive localized edema. The reduction of edema may be possible with the delivery of agents to promote lymphangiogenesis and drain localized edema or toxin buildup from the airway tissues. Parasympathetic nerve responses or hyper-reactivity of airways to environmental stimulus may be reduced by the delivery of localized denervation agents.

Many current devices and methods, however, can be less than ideal for safely, reliably, and/or effectively delivering therapeutic agents to the bronchial wall. Drugs such as mitomycin, paclitaxel, and other anti-neoplastic agents, have been swabbed on the epithelial surface of the bronchus but retention of the swabbed drug may be less than ideal in at least some instances. Disadvantages of current clinical practice paradigms, include systemic and inhaled medications, may include overall side effects from increased absorption and decreased local concentration in the targeted area as many of these bronchial diseases are localized in situ. Thus, it would be desirable to provide improved medical devices, methods, and systems for the local delivery of therapeutic agents into the bronchial wall and other bodily lumens.

BRIEF SUMMARY OF THE INVENTION

The present invention provides catheters with a single balloon or other inflatable actuator which is inflated at a first pressure to unfurl or deploy a first portion of the balloon, where delivery of an additional inflation pressure or volume expands or otherwise deploys a second portion of the balloon wall to a size larger than or a configuration different than that achievable by inflation or unfurling of the first portion of the balloon wall alone. Multiple components may be combined into the same balloon or pressure component, such that one part of the wall is non-distensible and another part of the wall is compliant or elastomeric, such that a single inflation step, whether it involves volume or pressure, may be useful to activate both the non-distensible and compliant structures simultaneously or in series.

The present invention also provides catheters and methods for deploying interventional tools in blood vessels and other body lumens. The interventional tools are typically needles which are penetrated into a luminal wall, but could be other structures such as atherectomy blades, optical fibers for delivering laser energy, mechanical abrasion and drilling components, and the like. The catheters comprise a catheter body having a proximal end and a distal end. The needle or other interventional tool is coupled to a distal portion of the catheter, and an inflatable structure is provided on or near the distal portion of the catheter body in order to advance the tool laterally relative to an axis of the catheter body. The inflatable structure may comprise two or more discrete regions which deform or inflate at different, typically successive inflation pressures. Usually, the regions will have different elasticities (where one may be substantially non-elastic or non-distensible), but in certain embodiments the regions could have identical elasticities where inflation of one or more of the regions below threshold pressure is prevented by tethers or other restraints which yield or break above said threshold pressure(s). By providing at least one non-distensible region, the non-distensible region can be fully inflated at relatively low pressures to a preselected size. If additional force or lateral displacement is needed, the inflatable structure can then be inflated beyond the first inflation threshold in order to expand one or more additional regions of the balloon, where the additional regions may have the same inflation characteristics or different inflation characteristics.

The regions of differing elasticity in the inflation structure can be achieved and fabricated in a variety of ways. In the exemplary embodiments below, the regions are formed in an edge-to-edge manner or along an overlapping border region using conventional masking and deposition techniques. It will be appreciated that the regions could also be formed by layering materials of differing elasticities, providing layers having different thicknesses, providing reinforcement fibers or materials which create regions of different elasticity within a matrix of the same material, providing tethers and other stretchable or breakable elements within regions of the inflation structure which yield or break when tension is applied above threshold levels, and the like.

The interventional tool may be mounted directly on the catheter body, but in the illustrated embodiments is mounted on the inflatable structure itself. It will be appreciated that more than one interventional tool may be mounted on the catheter, and that such multiple tools may be mounted directly on the catheter body, on the inflatable structure, or both.

By "non-distensible," it is meant that the material of the balloon will be inflatable from a lower profile or volume configuration to an expanded or higher profile or volume configuration. Once at the higher volume, expanded configuration, however, the material will no longer stretch or expand to any reasonable extent (typically less than 200% elongation in any direction prior to rupture) even though the inflation pressure can be raised significantly above the threshold pressure which achieves the higher volume inflation. By "elastomeric" it is meant that the material displays elasticity as more pressure is applied. Usually, there will be minimum or nominal stretching or expansion at or below the threshold pressure, but significant stretching and expansion at inflation pressures above the threshold pressure (typically at least 50% elongation in any direction prior to rupture, often at least 300% elongation in any direction prior to rupture, and usually at least greater than the elongation achievable by the non-distensible material prior to rupture). Additionally, the elastomeric materials will continue to stretch, usually in a nonlinear manner as pressure is increased above the threshold level.

The present invention further provides methods for treating body lumens comprising introducing one or more interventional tools to the body lumen. An inflatable structure is inflated to a first pressure below a threshold pressure to advance the tool laterally to a first "maximum" distance which will not be exceeded so long as the pressure is maintained below the threshold pressure level. After inflation to the first pressure, if it is desired to further laterally advance the intervention tool, the inflatable structure may be inflated to a pressure which exceeds the first threshold pressure to further laterally advance the tool beyond the first maximum distance. The tool may be advanced to a second maximum distance, or alternatively may be incrementally advanced if the inflatable structure includes an elastic region which expands in linear or nonlinear proportion to the inflation pressure.

Such methods may be used to treat many diseases. In particular, such methods may be used to treat bronchial carcinoma or to maintain patency in a patient's bronchus which has had a bronchial carcinoma in the bronchus debulked (i.e., the bronchus has be recanalized). A catheter having the inflatable structure at its distal end can be positioned within the bronchus of the patient. A target region of one or more of a bronchial wall, submucosa, media, and adventitia can then be punctured at or adjacent a location of the debulked bronchial carcinoma with an injection needle disposed on the distal end of the catheter. And, an amount of a cytotoxic, cytostatic, or anti-neoplastic agent, such as paclitaxel, can be delivered to the target region through the injection needle. The delivered amount of cytotoxic, cytostatic, or anti-neoplastic agent may be effective to limit recurrent bronchial occlusion due to recurrence of the bronchial carcinoma by a therapeutically beneficial amount.

Such methods may also be used to treat diseases including asthma, chronic obstructive pulmonary disease (COPD), bronchitis, mucous hypersecretion, cystic fibrosis, tracheobronchomalacia or excessive dynamic airway collapse (EDAC). As examples, in the case of tracheobronchomalacia or EDAC, an airway has lost its rigidity. Agents such as bulking agents used in the common practice of plastic surgery (for example, Artefill®), sclerosing or fibrosing agents that can stiffen tissues, collagen, thermoset polymers, or the like can be delivered to the airway wall to provide stiffness without placing a stent in the lumen of the airway. In the case of bronchitis, localized antibiotics, anti-infectives, or steroids may be given to reduce the inflammation of the bronchus. With mucous hypersecretion or cystic fibrosis, agents may be delivered to reduce the hypersecretive process of mucous generation. With asthma or COPD, agents can be delivered to reduce edema, reduce hyperactivity of smooth muscle (such as by paralysis, lesioning, deadening), or reduce activity of sympathetic, parasympathetic or sensory nerves.

In a first aspect of the present invention, a medical device comprises a tubular member with a proximal and distal end, an involuted balloon at or near the distal end of the medical device with a working component embedded in the involuted segment, an ability to inflate the involuted balloon to deploy the working component, and a material with lower modulus than the involuted balloon material, affixed to and comprising part of the wall of the involuted structure, such that the lower modulus material may expand at a different rate and create an anchoring or opposing force to the working component. The material with lower modulus may be affixed in one or more ways to the material with higher modulus. In most cases, the lower modulus material resembles a "patch", or membrane structure, on the opposite side of the involuted structure from the working component.

In a second aspect of the present invention similar to the first aspect, the medical device comprises a tubular member with proximal and distal end, a working component at the distal end, and the requirement to place such working component asymmetrically against the wall of a body lumen. The attachment of the lower modulus "patch" to one side of the working component end structure allows for the asymmetric deployment of the working component via hydraulic or pneumatic pressurization of the lower modulus patch, or membrane, with respect to the higher modulus flexible but relatively non-distensible structure to which it is attached.

In a third aspect of the present invention, the working end of the tubular medical device may require particular positioning within a body lumen. Multiple low-modulus "patch", or membrane, structures may be affixed to a higher modulus structure such that the patches may be inflated individually or simultaneously in order to position the tip of the medical device appropriately within the body lumen.

In a fourth aspect of the present invention, the lower modulus "patch" or membrane structure and the higher modulus flexible but relatively non-distensible "anchor" structure meet at a joint that is formed between and consists only of the two materials constituting the patch and the anchor, respectively. The seal formed between the two materials at this joint is free from leakage below a particular amount of pressurization, and thus integrates the two materials to form one pressure vessel with wall components comprised of each material.

In a fifth aspect of the present invention, when the pressure vessel is pressurized and inflated to deploy a needle into the wall of the airway, the base around the needle is caused to seal itself against the airway wall, which prevents leakage of fluid delivered through the needle back into the airway.

In an exemplary embodiment, the low-modulus material (the patch) is a flexible material such as silicone rubber or polydimethylsiloxane (PDMS). The high-modulus material (which can form the anchor to the patch or membrane) is a more flexible but relatively non-distensible polymer such as poly-paraxylylene (parylene N, C, or D). The low modulus material may be generally in a round and flat configuration, but may have more complex shape. The high modulus material is designed to have a "hole" in it approximately the size of the patch material, with some overlap to accommodate the attachment joint. The silicone patch, or membrane, and parylene flexible but relatively non-distensible material may be fixedly attached by polymeric encapsulation or polymeric adhesion, a process in which the parylene is vapor-deposited directly onto three substrates at once: a removable mold material adjacent to the silicone patch, the edge or border region of the silicone patch, and a removable (masking) material that protects the remainder of the silicone patch from being coated. When both removable materials are removed (e.g. by dissolution), the remaining structure is a parylene substrate with an affixed silicone patch, in which the joint formed between the two component structures consists only of the two constituent materials that comprise the individual components.

In the embodiment described above, the silicone patch may be on the back side of a folded balloon structure. The folded balloon structure is primarily comprised of parylene, but the patch comprises at least some of the surface area of the balloon. When the balloon is inflated, the flexible but relatively non-distensible structure unfolds, and then the elastomeric silicone expands due to pressurization. The flexible but relatively non-distensible parylene material unravels, but stretches much less than the silicone, thus forming the dual modulus balloon.

In a further embodiment of the present invention, polymer vapor deposition may be used to form both the flexible but relatively non-distensible material component and a joint or interfacial region between the flexible component and the elastomeric component. Polymer vapor deposition of parylene or other suitable polymer typically begins with sublimation of a parylene dimer or other precursor at an elevated temperature in a low pressure chamber. The dimer vapor is then cleaved into monomer vapor as it travels through a higher temperature furnace. The monomer vapor travels into a deposition chamber, also held under vacuum, but at ambient temperature, at which point the monomer molecules rapidly lose energy and polymerize on surfaces within the deposition chamber. This process creates parylene coatings on components placed into the deposition chamber. Parylene coatings are usually nearly uniform, but thickness of the films varies based on the thermal properties of the system, the amount of dimer used, the intricacy of geometric surfaces placed into the deposition chamber, and the pressure at which the coating process is performed. By properly masking and creating layers, as described hereinafter, the flexible component and the elastomeric component may be joined as the flexible component is being formed. Other variables of the coating process also add to variance in the parylene coating characteristics.

In further exemplary embodiments, the lower-modulus material may be polyether block amide (Pebax), neoprene, Silastic®, chronoprene, C-flex, latex or other elastomeric materials.

In further exemplary embodiments, the higher-modulus material may be a thermoplastic polymer such as polyimide, polyethylene, polypropylene, polyethyl teraphthalate (PET), PTFE (Teflon©), PEEK, Tygon, nylon, acetal or other materials, including polymers, semiconductors, or metals, typically employed in the manufacture of medical devices and products.

In further exemplary embodiments, the attachment joint between the low modulus and high modulus material may be formed by polymer fusion at high temperature or pressure, by the use of adhesives such as cyanoacrylate, or by techniques employing surface preparation by electron bombardment of both materials and then placement of the materials in contact with each other. All of the above may be used to form leak-free seal joints between the low modulus and high modulus materials.

In further exemplary embodiments, the balloon that is formed from the low modulus and high modulus materials, when expanded, forms a seal around the base of the needle and the bronchial wall, which prevents leakage of injectable materials out from the needle hole that is created in the bronchus.

Aspects of the present disclosure also provide a method of maintaining bronchial patency in a bronchus of a patient. The method comprises delivering an amount of a therapeutic agent to tissue surrounding the bronchus. The delivered amount is effective to limit recurrent bronchial occlusion by a therapeutically beneficial amount. Delivery comprises injecting the amount of the therapeutic agent into one or more of a bronchial wall, submucosa, media, or adventitia of the bronchus.

In many embodiments, the amount of the therapeutic agent is delivered to a site at or adjacent a cancerous tumor. The cancerous tumor may comprise a bronchia carcinoma, granuloma, fibrosis, or benign or malignant structure or narrowing. The amount of therapeutic agent may be delivered to the site at or adjacent a cancerous tumor which will typically have been debulked prior to delivery of the therapeutic agent. The delivered amount of therapeutic agent will typically be effective to prevent the recurrence of the cancerous tumor.

The therapeutic agent may be delivered through various steps. A needle may be positioned through a wall of the bronchus so that an aperture of the needle is positioned at or beyond the bronchial adventitia. The needle may comprise a 25 to 45 gauge needle, preferably 45 gauge. The penetration of the therapeutic agent through the tissue may be confirmed by imaging either the therapeutic agent mixed with a diagnostic agent or by delivery of a diagnostic agent prior to the delivery of the therapeutic agent.

In many embodiments, the method may further comprises steps of advancing a catheter into the bronchus and positioning the catheter adjacent a target region of the bronchial wall and adventitia before delivery of the therapeutic agent. A further step may include the expansion of an expandable element disposed on a distal end of the positioned catheter to cause a needle disposed on the expandable element to puncture the target region of the bronchial wall, submucosa, media, or adventitia before delivery of the therapeutic agent. The expandable element may comprise an inflatable balloon, and expansion of the expandable element may occur by inflation, preferably by air, but alternatively or in combination by saline or other buffers. The inflatable balloon may be inflated with 2 atmospheres of pressure without damaging the bronchus.

The therapeutic agent will typically comprise a cytotoxic, cytostatic, or anti-neoplastic agent. The therapeutic agent will often comprise paclitaxel. In some embodiments, the therapeutic agent comprises Abraxane®, a branded formulation of paclitaxel available from Celgene Corp. of Summit, N.J. The cytotoxic, cytostatic, or anti-neoplastic agent for delivery may have a concentration in the range of 0.05 mg/mL to 2.5 mg/mL, such as less than or equal to about 1.5 mg/mL or 0.5 mg/mL. Studies have been conducted that indicate the safety of a 1.5 mg/mL or less dosage and also strongly suggest both safety and efficacy for the local delivery of such a dosage to treat bronchial carcinomas and/or maintain airway patency by reducing their recurrence.

Other potential therapeutic agents include chemotherapeutic agents, specifically those cytotoxic agents traditionally used to treat cancer. Such agents may include, but are not limited to, alkylating agents such as busulfan, hexamethylmelamine, thiotepa, cyclophosphamide, mechlorethamine, uramustine, melphalan, chlorambucil, carmustine, streptozocin, dacarbazine, temozolomide, ifosfamide, and the like; anti-neoplastic agents such as mitomycin C and the like; anti-metabolites such as methotrexate, azathioprine, mercaptopurine, fludarabine, 5-fluorouracial, and the like; platinum-containing anti-cancer agents such as cisplatin, carboplatin and the like; anthracyclines such as daunorubicin, doxorubicin, epirubicin, idarubicin, mitoxantrone, and the like; plant alkaloids and terpenoids such as vincristine, vinblastine, vinorelbine, vindesine, podophyllotoxin, doclitaxel, and the like; topoisomerase inhibitors such as irinotecan, amsacrine, topotecan, etoposide, teniposide, and the like; antibody agents, such as rituximab, trastuzumab, bevacizumab, erlotinib, dactinomycin; finasteride; aromatase inhibitors; tamoxifen; goserelin; imatinib mesylate.

Other pulmonary diseases such as asthma, reactive airway disease, tachypnea, fibrotic lung diseases such as idiopathic pulmonary fibrosis and asbestosis, cystic fibrosis, interstitial lung disease, chemical pneumonitis, desquamative interstitial pneumonitis, non-specific interstitial pneumonitis, lymphocytic interstitial pneumonitis, usual interstitial pneumonitis, idiopathic pulmonary fibrosis, pulmonary edema, aspiration, asphyxiation, pneumothorax, right-to-left shunts, left-to-right shunts, respiratory failure, pneumonia, chronic obstructive pulmonary disease, emphysema, bronchitis, bronchopulmonary dysplasia, lung cancer, and the like may be treated by the devices, methods, and systems provided herein. Many of these diseases may involve the reduction of bronchial patency, for example, which can be treated by the devices, methods, and systems provided herein.

Aspect of the present disclosure also provide a method of maintaining patency in a patient's bronchus which has had a bronchial carcinoma in the bronchus debulked. A catheter is positioned within the bronchus of the patient. A target region of one or more of a bronchial wall, submucosa, media, and adventitia is punctured at or adjacent a location of the debulked bronchial carcinoma with an injection needle disposed on a distal end of the catheter. And, an amount of a cytotoxic, cytostatic, or anti-neoplastic agent is delivered to the target region through the injection needle. The delivered amount of cytotoxic, cytostatic, or anti-neoplastic agent is effective to limit recurrent bronchial occlusion due to recurrence of the bronchial carcinoma by a therapeutically beneficial amount.

The cytotoxic, cytostatic, or anti-neoplastic agent often comprises paclitaxel. In some embodiments, the cytotoxic, cytostatic, or anti-neoplastic agent for delivery may comprise Abraxane®, a branded formulation of paclitaxel. The target region is typically punctured with the injection needle by expanding an expandable element disposed on a distal end of the positioned catheter. The expandable element may comprise an inflatable balloon and expanding the expandable element may comprise inflating the balloon preferably as with air, or alternatively or in combination with saline or other buffers. The cytotoxic, cytostatic, or anti-neoplastic agent for delivery typically has a concentration in the range of 0.05 mg/mL to 2.5 mg/mL, such as less than or equal to about 1.5 mg/mL or 0.5 mg/mL. The injection needle may comprise a 25 to 45 gauge needle, preferably a 45 gauge needle.

Aspects of the present disclosure also provide a therapeutic agent for use in maintaining patency in a bronchus of a patient. The therapeutic agent may be delivered in a therapeutically beneficial amount effective to limit recurrent bronchial occlusion. The therapeutic agent may be delivered into one or more of a bronchial wall, submucosa, media, or adventitia of the bronchus.

The therapeutically beneficial amount of the therapeutic agent may be delivered to a site at or adjacent a cancerous tumor. The cancerous tumor may comprise a bronchia carcinoma, granuloma, fibrosis, or benign or malignant structure or narrowing. The therapeutically beneficial amount of the therapeutic agent may be delivered to a site at or adjacent a cancerous tumor which may have been debulked prior to delivery of the therapeutic agent. The therapeutically beneficial amount of the therapeutic agent may be effective to prevent the recurrence of the cancerous tumor.

The therapeutically beneficial amount of the therapeutic agent may be delivered through a needle positioned through a wall of the bronchus so that an aperture of the needle is positioned at or beyond the bronchial adventitia. The needle may comprise a 25 to 45 gauge needle.

The penetration of the tissue by the therapeutic agent may be confirmed by imaging either the therapeutic agent mixed with a diagnostic agent or by delivery of a diagnostic agent prior to the delivery of the therapeutic agent.

The therapeutic agent may be delivered through a catheter advanced into the bronchus. The catheter may be positioned adjacent a target region of the bronchial wall and adventitia before delivery of the therapeutic agent. The catheter may comprise an expandable element disposed on a distal end thereof and a needle disposed on the expandable element. The expandable element may be expandable to cause the needle to puncture the target region of the bronchial wall, submucosa, media, or adventitia before delivery of the therapeutic agent. The expandable element may comprise an inflatable balloon. The inflatable balloon may be inflatable with 2 atmospheres of pressure without damaging the bronchus. The inflatable balloon may preferably be inflated with air or alternatively or in combination may be inflated with saline or other buffers.

The therapeutic agent may comprise a cytotoxic, cytostatic, or anti-neoplastic agent such as paclitaxel or Abraxane®. The therapeutic agent that is delivered may have a concentration in the range of 0.05 mg/mL to 2.5 mg/mL, a concentration of less than or equal to about 1.5 mg/mL, or a concentration of less than or equal to about 0.5 mg/mL.

Aspects of the present disclosure also provide a system for use in maintaining patency in a bronchus of a patient. The system may comprise a therapeutic agent, a catheter configured to be placed within a bronchus of the patient, an expandable element disposed on a distal end of the catheter, an expandable element disposed on a distal end of the catheter, and an injection needle coupled to the expandable element. Expanding the expandable element may advance the injection needle in a direction transverse to a longitudinal axis of the catheter to puncture a target region of one or more of a bronchial wall, submucosa, media, and adventitia. The expandable element may comprise an inflatable balloon which may be inflated with air or alternatively or in combination inflated with saline or other buffers. When the needle has punctured the target region, the needle may deliver an amount of the therapeutic agent to the target region, and the amount may be effective to limit recurrent bronchial occlusion. The target region may be at or adjacent a location of a previously debulked bronchial carcinoma in the bronchus. The amount of therapeutic agent delivered may be effective to limit recurrent bronchial occlusion due to recurrence of the bronchial carcinoma by a therapeutically beneficial amount.

The therapeutic agent may comprise a cytotoxic, cytostatic, or anti-neoplastic agent such as paclitaxel or Abraxane®. The therapeutic agent that is delivered may have a concentration in the range of 0.05 mg/mL to 2.5 mg/mL, a concentration of less than or equal to about 1.5 mg/mL, or a concentration of less than or equal to about 0.5 mg/mL.

Aspects of the present disclosure also provide a device, a therapeutic agent, a system and a method to treat malacia of the trachea or bronchus, or excessive dynamic airway collapse (EDAC), with the use of stiffening agents delivered directly into the wall of the airway. In the case of malacia or EDAC, the bronchial or tracheal wall has become floppy and the patency of the airway is not maintained with exhalation, which can cause cough, irritation, inflammation, or infection of the airway. These conditions may happen in pediatric patients due to congenital anomalous lack of cartilage formation, or in adults due to chronic obstructive pulmonary disease (COPD) or for idiopathic reasons, although that is rare. Stiffening of the airway wall may comprise the injection of polymers, hydrogels, biologic materials (such as collagen), bone cement, artificial cartilage, or sclerosing agents that lead to fibrosis and stiffening of the bronchial tissues. The amount of agent delivered may be in the range of 0.1 mL to 3 mL per injection, and may be placed in several injections sites along the length of an airway that is compromised. For example, an amount of agent may be injected at a first location in the trachea or bronchus and then at a second location in the trachea or bronchus diametrically opposed to the first location. In other examples, injections may be performed serially up and down the bronchus or trachea, wherein each injection would spread circumferentially around the airway to provide a support structure to the airway wall and prevent its collapse. The needle may be placed submucosally but radially inward from the outside of the bronchial or tracheal wall or the parenchyma of the lung. In yet other examples, similar procedures may be used to inject stiffening agents into the esophageal wall.

Aspects of the present disclosure also provide a polymer precursor for use in a method of maintaining patency in a trachea or a bronchus of a patient. Said polymer precursor may be for delivery to tissue in the trachea or bronchus. The polymer precursor can at least partially solidify in the tissue to provide support for the trachea or bronchus to maintain patency in the trachea or bronchus. Any of the catheter devices or systems disclosed herein may be used to deliver said polymer precursor.

Aspects of the present disclosure also provide a polymer precursor for use in a method of maintaining patency in a trachea or a bronchus of a patient. The method may comprise a step of delivering an amount of a polymer precursor to tissue in the trachea or bronchus. Any of the catheter devices or systems disclosed herein may be used to deliver said polymer precursor. The polymer precursor may at least partially solidify in the tissue to provide support for the trachea or bronchus to maintain patency in the trachea or bronchus. The polymer precursor may be for delivery into one or more of a wall, submucosa, lamina, media, or adventitia of the trachea or bronchus. The delivery may be by injection. The method may further comprise a step of confirming that said polymer precursor is penetrating said tissue by imaging either the polymer precursor mixed with a diagnostic agent or by a diagnostic agent pre-delivered prior to the delivery of the polymer precursor. The delivery may comprise steps of advancing a catheter into an airway of the trachea or bronchus and positioning the catheter adjacent a target region of the tracheal or bronchial wall and adventitia before delivery of the polymer precursor. To deliver the amount of the polymeric precursor, an expandable element disposed on a distal end of the positioned catheter may be expanded to cause a needle disposed on the expandable element to puncture the target region of the wall, submucosa, media, or adventitia of the trachea or bronchus before delivery of the polymeric precursor. Said prepolymer precursor may be for deliver via a catheter which has been pre-positioned as defined in any of the steps defined above.

Aspects of the present disclosure also provide a device comprising (a) a polymer precursor, (b) a catheter, (c) an expandable element disposed on a distal end of said catheter, and (d) a needle disposed on said expandable element. The expandable element may comprise an inflatable balloon. The inflatable balloon may be suitable for inflation with air, saline, or a buffer.

DETAILED DESCRIPTION OF THE INVENTION

By way of example, the first eight figures illustrate a needle injection catheter that can benefit from the dual modulus balloon offered by the present invention.

Figure 1A:
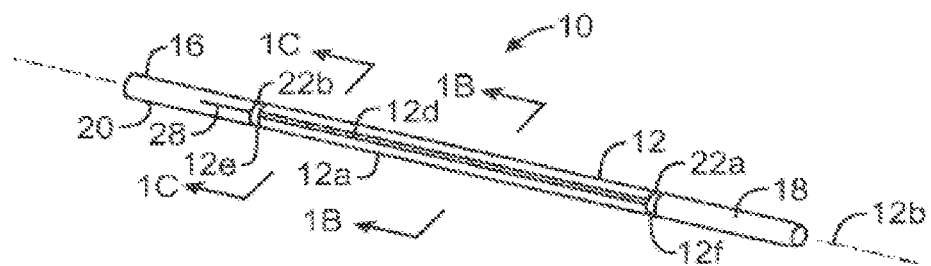
FIG. 1A is a schematic, perspective view of an intraluminal injection catheter suitable for use in the methods and systems of the present invention.
Figure 1B:
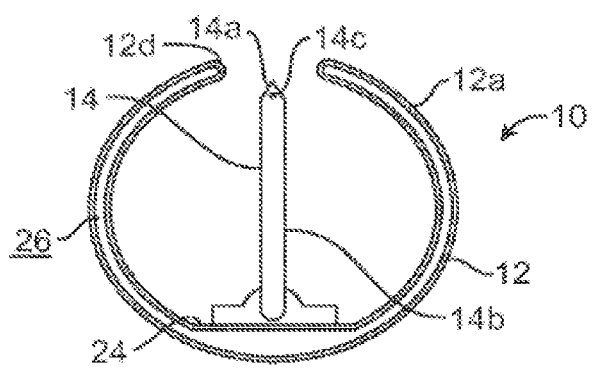
FIG. 1B is a cross-sectional view along line 1B-1B of FIG. 1A.
Figure 1C:
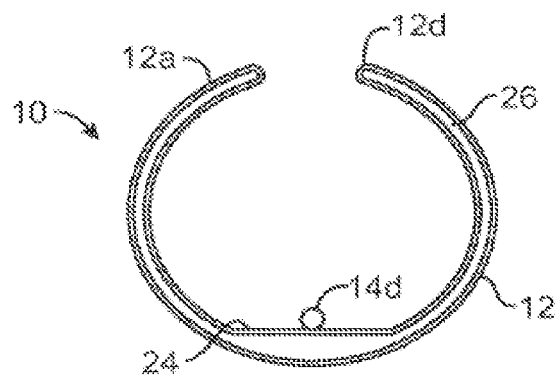
FIG. 1C is a cross-sectional view along line 1C-1C of FIG. 1A.
Figure 2A:
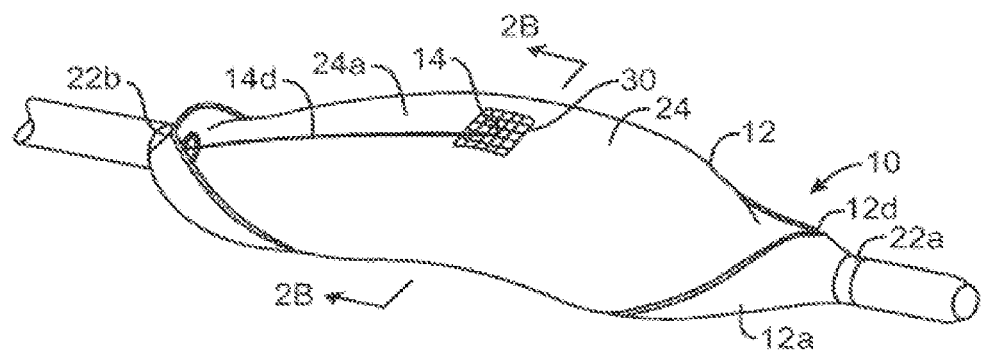
FIG. 2A is a schematic, perspective view of the catheter of FIGS. 1A-1C shown with the injection needle deployed.
Figure 2B:
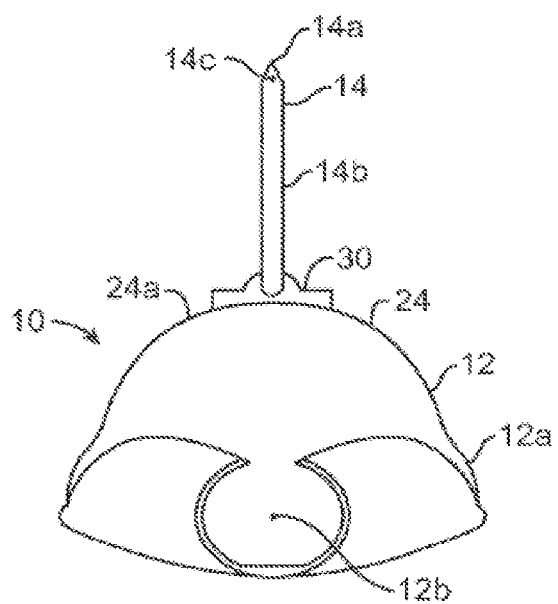
FIG. 2B is a cross-sectional view along line 2B-2B of FIG. 2A.

As shown in FIGS. 1A-2B, a microfabricated intraluminal catheter 10 includes an actuator 12 having an actuator body 12a and central longitudinal axis 12b. The actuator body more or less forms a C-shaped outline having an opening or slit 12d extending substantially along its length. A microneedle 14 is located within the actuator body, as discussed in more detail below, when the actuator is in its unactuated condition (furled state) (FIG. 1B). The microneedle is moved outside the actuator body when the actuator is operated to be in its actuated condition (unfurled state) (FIG. 2B).

The actuator may be capped at its proximal end 12e and distal end 12f by a lead end 16 and a tip end 18, respectively, of a therapeutic catheter 20. The catheter tip end serves as a means of locating the actuator inside a body lumen by use of a radio opaque coatings or markers. The catheter tip also forms a seal at the distal end 12f of the actuator. The lead end of the catheter provides the necessary interconnects (fluidic, mechanical, electrical or optical) at the proximal end 12e of the actuator.

Retaining rings 22a and 22b are located at the distal and proximal ends, respectively, of the actuator. The catheter tip is joined to the retaining ring 22a, while the catheter lead is joined to retaining ring 22b. The retaining rings are made of a thin, on the order of 10 to 100 microns (μm), substantially flexible but relatively non-distensible material, such as Parylene (types C, D or N), or a metal, for example, aluminum, stainless steel, gold, titanium or tungsten. The retaining rings form a flexible but relatively non-distensible substantially "C"-shaped structure at each end of the actuator. The catheter may be joined to the retaining rings by, for example, a butt-weld, an ultra sonic weld, integral polymer encapsulation or an adhesive such as an epoxy.

The actuator body further comprises a central, expandable section 24 located between retaining rings 22a and 22b. The expandable section 24 includes an interior open area 26 for rapid expansion when an activating fluid is supplied to that area. The central section 24 is made of a thin, semi-flexible but relatively non-distensible or flexible but relatively non-distensible, expandable material, such as a polymer, for instance, Parylene (types C, D or N), silicone, polyurethane or polyimide. The central section 24, upon actuation, is expandable somewhat like a balloon-device.

The central section is capable of withstanding pressures of up to about 200 psi upon application of the activating fluid to the open area 26. The material from which the central section is made of is flexible but relatively non-distensible or semi-flexible but relatively non-distensible in that the central section returns substantially to its original configuration and orientation (the unactuated condition) when the activating fluid is removed from the open area 26. Thus, in this sense, the central section is very much unlike a balloon which has no inherently stable structure.

The open area 26 of the actuator is connected to a delivery conduit, tube or fluid pathway 28 that extends from the catheter's lead end to the actuator's proximal end. The activating fluid is supplied to the open area via the delivery tube. The delivery tube may be constructed of Teflon© or other inert plastics. The activating fluid may be a saline solution or a radio-opaque dye.

The microneedle 14 may be located approximately in the middle of the central section 24. However, as discussed below, this is not necessary, especially when multiple microneedles are used. The microneedle is affixed to an exterior surface 24a of the central section. The microneedle is affixed to the surface 24a by an adhesive, such as cyanoacrylate. Alternatively, the microneedle maybe joined to the surface 24a by a metallic or polymer mesh-like structure 30 (See FIG. 4), which is itself affixed to the surface 24a by an adhesive. The mesh-like structure may be-made of, for instance, steel or nylon.

The microneedle includes a sharp tip 14a and a shaft 14b. The microneedle tip can provide an insertion edge or point. The shaft 14b can be hollow and the tip can have an outlet port 14c, permitting the injection of a pharmaceutical or drug into a patient. The microneedle, however, does not need to be hollow, as it may be configured like a neural probe to accomplish other tasks.

As shown, the microneedle extends approximately perpendicularly from surface 24a. Thus, as described, the microneedle will move substantially perpendicularly to an axis of a lumen into which has been inserted, to allow direct puncture or breach of body lumen walls.

The microneedle further includes a pharmaceutical or drug supply conduit, tube or fluid pathway 14d which places the microneedle in fluid communication with the appropriate fluid interconnect at the catheter lead end. This supply tube may be formed integrally with the shaft 14b, or it may be formed as a separate piece that is later joined to the shaft by, for example, an adhesive such as an epoxy.

The needle 14 may be a 30-gauge, or smaller, steel needle. Alternatively, the microneedle may be microfabricated from polymers, other metals, metal alloys or semiconductor materials. The needle, for example, may be made of Parylene, silicon or glass. Microneedles and methods of fabrication are described in U.S. application Ser. No. 09/877,653, filed Jun. 8, 2001, entitled "Microfabricated Surgical Device", assigned to the assignee of the subject application, the entire disclosure of which is incorporated herein by reference.

Figure 3:
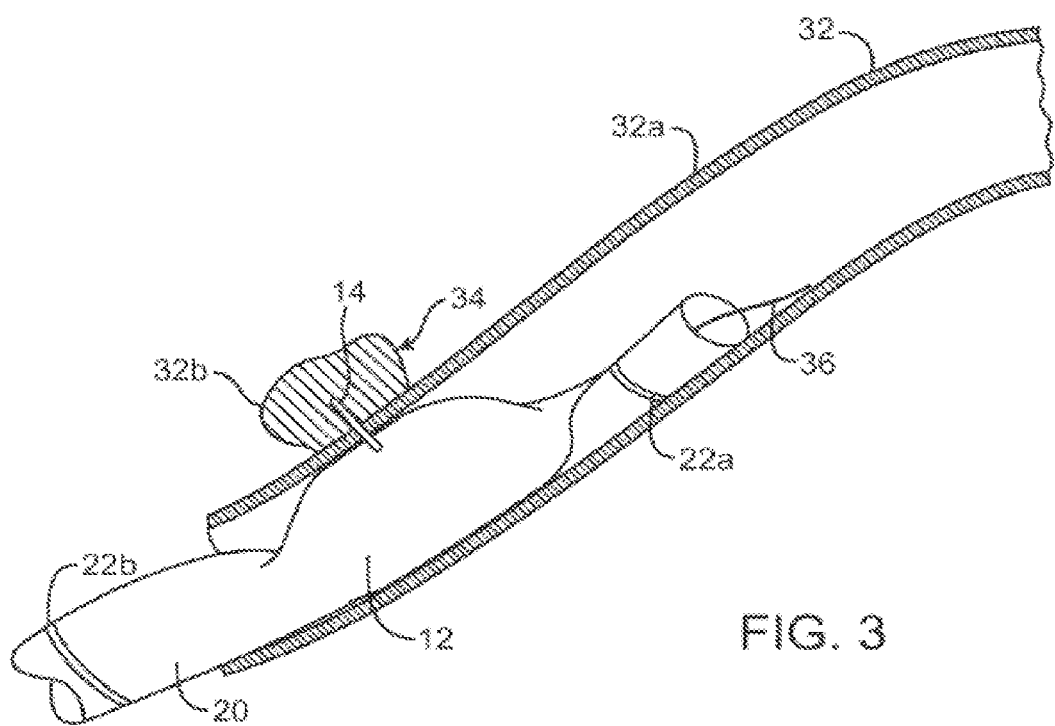
FIG. 3 is a schematic, perspective view of the intraluminal catheter of FIGS. 1A-1C injecting therapeutic agents into an adventitial space surrounding a body lumen in accordance with the methods of the present invention.

The catheter 20, in use, is inserted through an opening in the body (e.g. for bronchial or sinus treatment) or through a percutaneous puncture site (e.g. for artery or venous treatment) and moved within a patient's body passageways 32, until a specific, targeted region 34 is reached (see FIG. 3). The targeted region 34 may be the site of tissue damage or more usually will be adjacent the sites typically being within 100 mm or less to allow migration of the therapeutic or diagnostic agent. As is well known in catheter-based interventional procedures, the catheter 20 may follow a guide wire 36 that has previously been inserted into the patient. Optionally, the catheter 20 may also follow the path of a previously-inserted guide catheter (not shown) that encompasses the guide wire.

During maneuvering of the catheter 20, well-known methods of fluoroscopy or magnetic resonance imaging (MRI) can be used to image the catheter and assist in positioning the actuator 12 and the microneedle 14 at the target region. As the catheter is guided inside the patient's body, the microneedle remains unfurled or held inside the actuator body so that no trauma is caused to the body lumen walls.

After being positioned at the target region 34, movement of the catheter is terminated and the activating fluid is supplied to the open area 26 of the actuator, causing the expandable section 24 to rapidly unfurl, moving the microneedle 14 in a substantially perpendicular direction, relative to the longitudinal central axis 12b of the actuator body 12a, to puncture a body lumen wall 32a. It may take only between approximately 100 milliseconds and five seconds for the microneedle to move from its furled state to its unfurled state.

The ends of the actuator at the retaining rings 22a and 22b remain fixed to the catheter 20. Thus, they do not deform during actuation. Since the actuator begins as a furled structure, its so-called pregnant shape may exist as an unstable buckling mode. This instability, upon actuation, may produce a large-scale motion of the microneedle approximately perpendicular to the central axis of the actuator body, causing a rapid puncture of the body lumen wall without a large momentum transfer. As a result, a microscale opening is produced with very minimal damage to the surrounding tissue. Also, since the momentum transfer is relatively small, only a negligible bias force is required to hold the catheter and actuator in place during actuation and puncture.

The microneedle aperture, in fact, travels with such force that it can enter body lumen tissue 32b as well as the adventitia, media, or intima surrounding body lumens. Additionally, since the actuator is "parked" or stopped prior to actuation, more precise placement and control over penetration of the body lumen wall are obtained.

After actuation of the microneedle and delivery of the agents to the target region via the microneedle, the activating fluid is exhausted from the open area 26 of the actuator, causing the expandable section 24 to return to its original, furled state. This also causes the microneedle to be withdrawn from the body lumen wall. The microneedle, being withdrawn, is once again sheathed by the actuator.

Various microfabricated devices can be integrated into the needle, actuator and catheter for metering flows, capturing samples of biological tissue, and measuring pH. The device 10, for instance, could include electrical sensors for measuring the flow through the microneedle as well as the pH of the pharmaceutical being deployed. The device 10 could also include an intravascular ultrasonic sensor (IVUS) for locating vessel walls, and fiber optics, as is well known in the art, for viewing the target region. For such complete systems, high integrity electrical, mechanical and fluid connections are provided to transfer power, energy, and pharmaceuticals or biological agents with reliability.

By way of example, the microneedle may have an overall length of between about 200 and 3,000 microns (μm). The interior cross-sectional dimension of the shaft 14b and supply tube 14d may be on the order of 20 to 250 um, while the tube's and shaft's exterior cross-sectional dimension may be between about 100 and 500 μm. The overall length of the actuator body may be between about 5 and 50 millimeters (mm), while the exterior and interior cross-sectional dimensions of the actuator body can be between about 0.4 and 4 mm, and 0.5 and 5 mm, respectively. The gap or slit through which the central section of the actuator unfurls may have a length of about 4-40 mm, and a cross-sectional dimension of about 50-500 μm. The diameter of the delivery tube for the activating fluid may be about 100 μm. The catheter size may be between 1.5 and 15 French (Fr).

Variations of the invention include a multiple-buckling actuator with a single supply tube for the activating fluid. The multiple-buckling actuator includes multiple needles that can be inserted into or through a lumen wall for providing injection at different locations or times.

Figure 4:
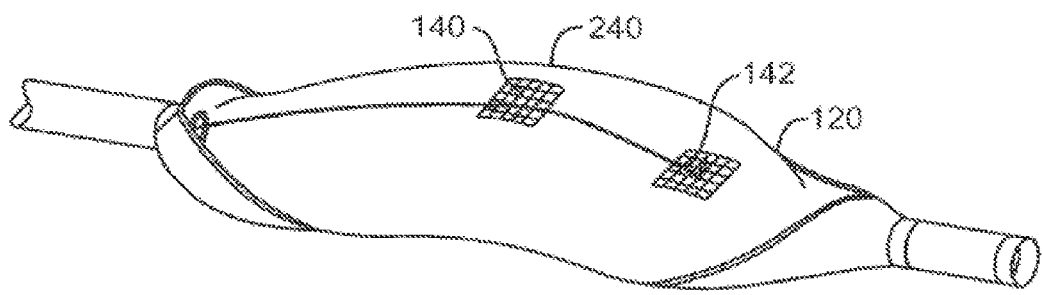
FIG. 4 is a schematic, perspective view of another embodiment of an intraluminal injection catheter useful in the methods of the present invention.

For instance, as shown in FIG. 4, the actuator 120 includes microneedles 140 and 142 located at different points along a length or longitudinal dimension of the central, expandable section 240. The operating pressure of the activating fluid is selected so that the microneedles move at the same time. Alternatively, the pressure of the activating fluid may be selected so that the microneedle 140 moves before the microneedle 142.

Specifically, the microneedle 140 is located at a portion of the expandable section 240 (lower activation pressure) that, for the same activating fluid pressure, will buckle outwardly before that portion of the expandable section (higher activation pressure) where the microneedle 142 is located. Thus, for example, if the operating pressure of the activating fluid within the open area of the expandable section 240 is two pounds per square inch (psi), the microneedle 140 will move before the microneedle 142. It is only when the operating pressure is increased to four psi, for instance, that the microneedle 142 will move. Thus, this mode of operation provides staged buckling with the microneedle 140 moving at time $t_1$, and pressure $p_1$, and the microneedle 142 moving at time $t_2$ and $p_2$, with $t_1$, and $p_1$, being less than $t_2$ and $p_2$, respectively.

This sort of staged buckling can also be provided with different pneumatic or hydraulic connections at different parts of the central section 240 in which each part includes an individual microneedle.

Figure 5:
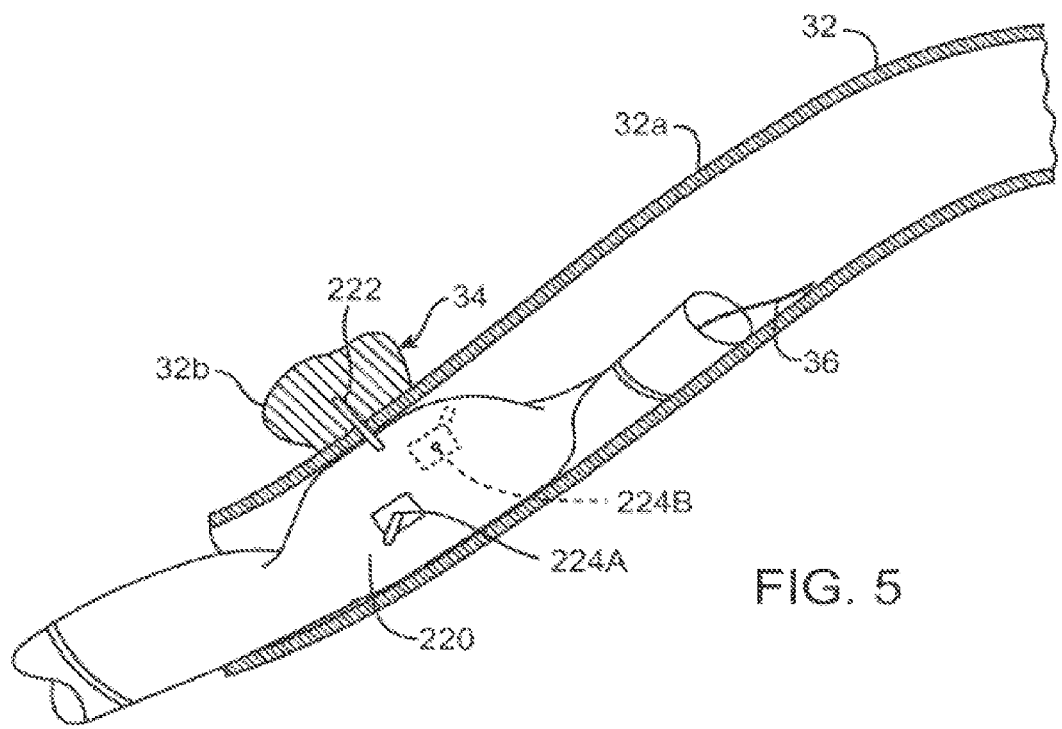
FIG. 5 is a schematic, perspective view of still another embodiment of an intraluminal injection catheter useful in the methods of the present invention, as inserted into one of a patient's body lumens.

Also, as shown in FIG. 5, an actuator 220 could be constructed such that its needles 222 and 224A move in different directions. As shown, upon actuation, the needles move at angle of approximately 90° to each other to puncture different parts of a lumen wall. A needle 224B (as shown in phantom) could alternatively be arranged to move at angle of about 180° to the needle 224A.

The above catheter designs and variations thereon, are described in published U.S. Patent Application No. 2003/0055400 (now U.S. Pat. No. 6,860,867, issued Mar. 1, 2005), the full disclosures of which are incorporated herein by reference. Co-pending and co-assigned application Ser. No. 10/350,314 (now lapsed but related to U.S. Pat. No. 7,744,584, (issued Jun. 29, 2010), U.S. Pat. No. 8,708,995 (issued Apr. 29, 2014), and U.S. Pat. No. 9,061,098 (issued Jun. 23, 2015)) describes the ability of substances delivered by direct injection into the adventitial and pericardial tissues of the heart to rapidly and evenly distribute within the heart tissues, even to locations remote from the site of injection.

The full disclosure of that co-pending application is also incorporated herein by reference. An alternative needle catheter design suitable for delivering the therapeutic or diagnostic agents of the present invention will be described below. That particular catheter design is described and claimed in co-assigned U.S. patent application Ser. No. 10/397,700 (now U.S. Pat. No. 7,141,041, issued on Nov. 28, 2006), filed on Mar. 19, 2003, the full disclosure of which is incorporated herein by reference.

Figure 6:
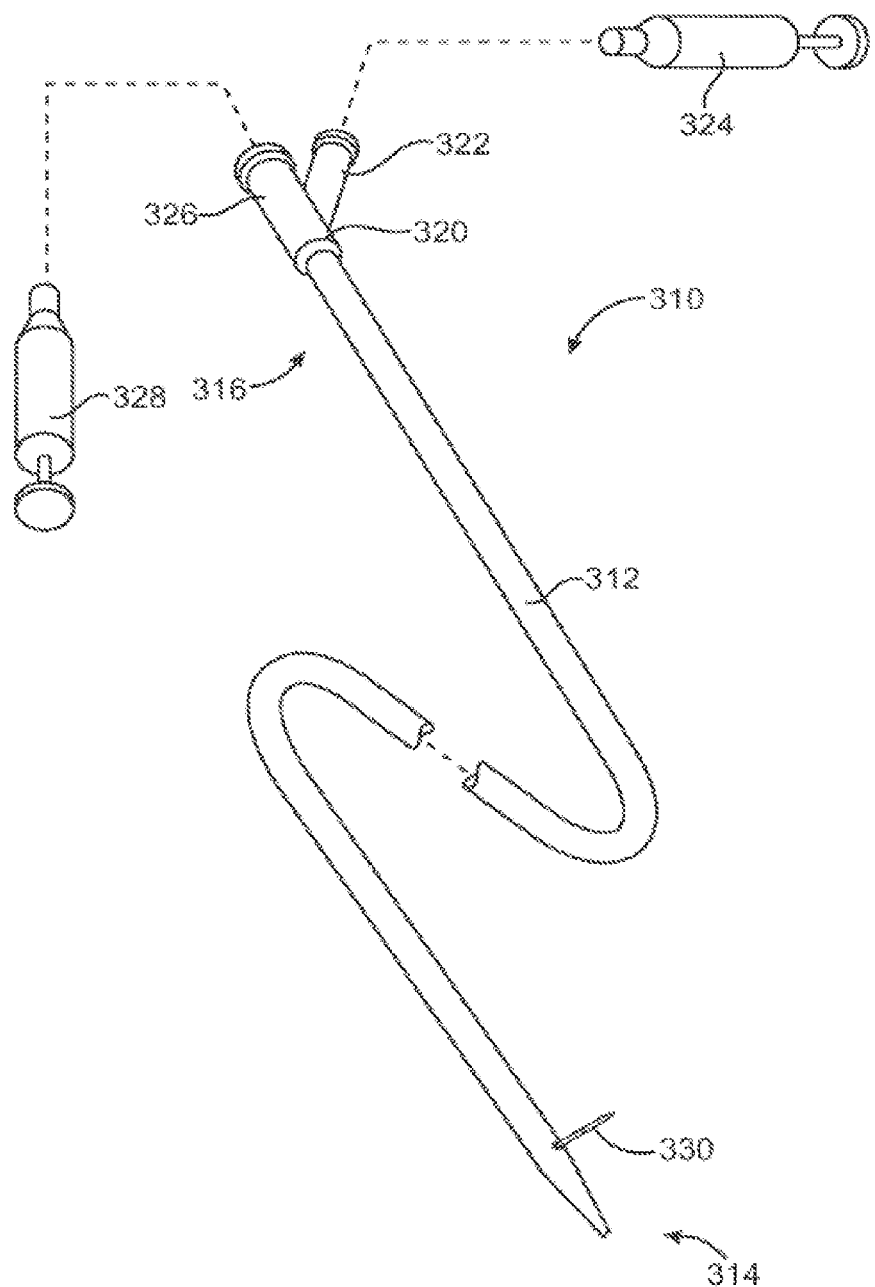
FIG. 6 is a perspective view of a needle injection catheter useful in the methods and systems of the present invention.

Referring now to FIG. 6, a needle injection catheter 310 constructed in accordance with the principles of the present invention comprises a catheter body 312 having a distal end 314 and a proximal 316. Usually, a guide wire lumen 313 will be provided in a distal nose 352 of the catheter, although over-the-wire and embodiments which do not require guide wire placement will also be within the scope of the present invention. A two-port hub 320 is attached to the proximal end 316 of the catheter body 312 and includes a first port 322 for delivery of a hydraulic fluid, e.g., using a syringe 324, and a second port 326 for delivering the pharmaceutical agent, e.g., using a syringe 328. A reciprocatable, deflectable needle 330 is mounted near the distal end of the catheter body 312 and is shown in its laterally advanced configuration in FIG. 6.

Figure 7:
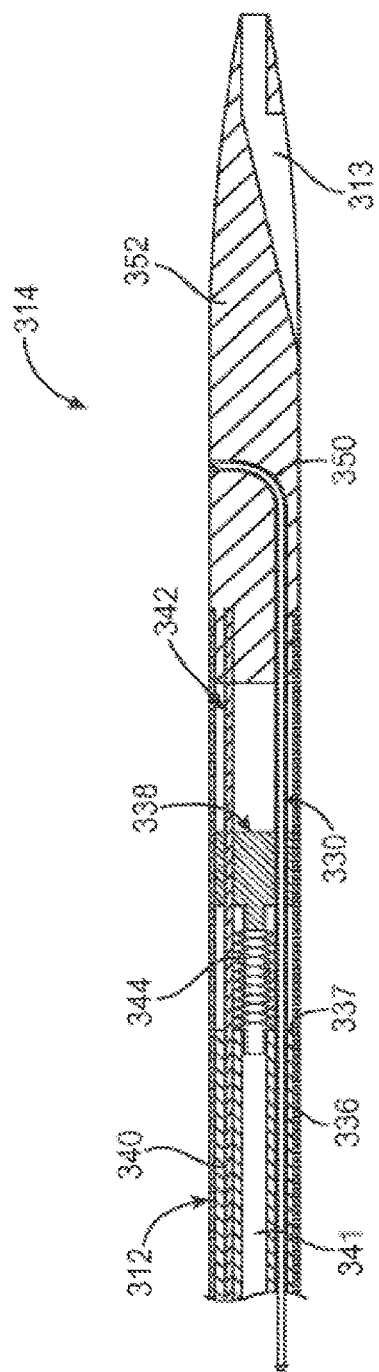
FIG. 7 is a cross-sectional view of the catheter FIG. 6 shown with the injection needle in a retracted configuration.

Referring now to FIG. 7, the proximal end 314 of the catheter body 312 has a main lumen 336 which holds the needle 330, a reciprocatable piston 338, and a hydraulic fluid delivery tube 340. The piston 338 is mounted to slide over a rail 342 and is fixedly attached to the needle 330. Thus, by delivering a pressurized hydraulic fluid through a lumen 341 tube 340 into a bellows structure 344, the piston 338 may be advanced axially toward the distal tip in order to cause the needle to pass through a deflection path 350 formed in a catheter nose 352.

Figure 8:
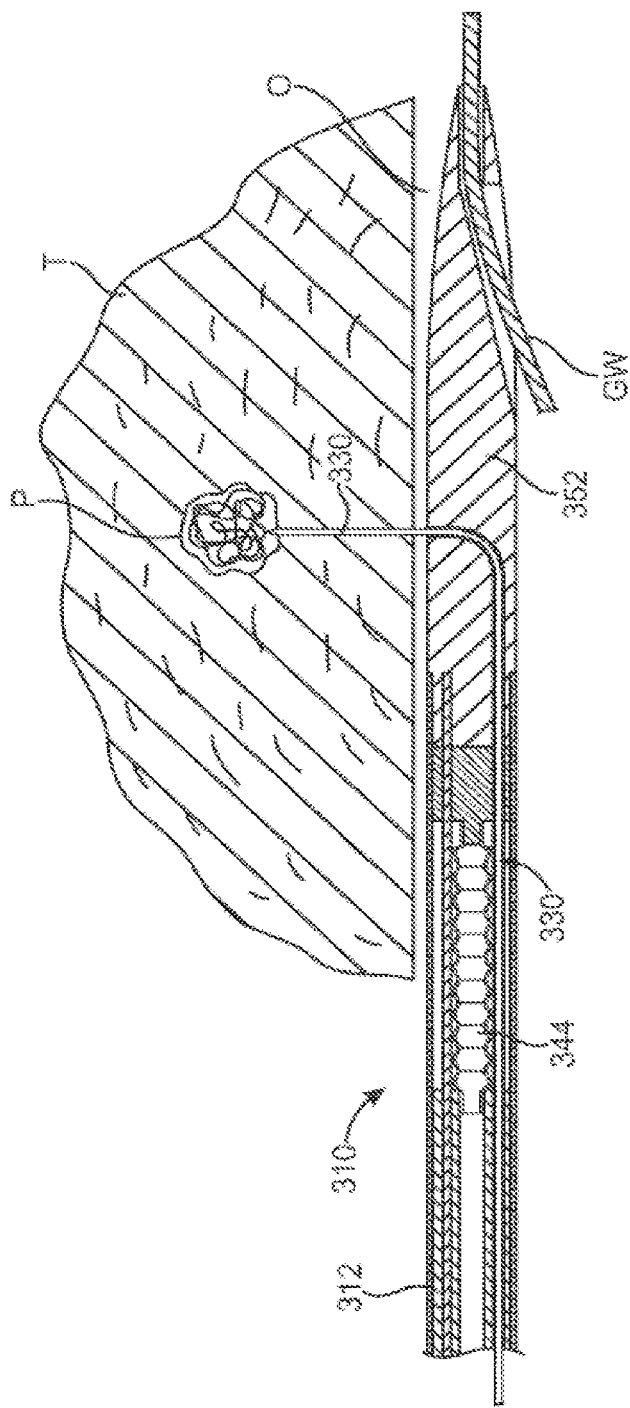
FIG. 8 is a cross-sectional view similar to FIG. 7, shown with the injection needle laterally advanced into luminal tissue for the delivery of therapeutic or diagnostic agents according to the present invention.

As can be seen in FIG. 8, the catheter 310 may be positioned in a coronary blood vessel BV, over a guide wire GW in a conventional manner. Distal advancement of the piston 338 causes the needle 330 to advance into luminal tissue T adjacent to the catheter when it is present in the blood vessel. The therapeutic or diagnostic agents may then be introduced through the port 326 using syringe 328 in order to introduce a plume P of agent in the cardiac tissue, as illustrated in FIG. 8. The plume P will be within or adjacent to the region of tissue damage as described above.

The needle 330 may extend the entire length of the catheter body 312 or, more usually, will extend only partially into the therapeutic or diagnostic agents delivery lumen 337 in the tube 340. A proximal end of the needle can form a sliding seal with the lumen 337 to permit pressurized delivery of the agent through the needle.

The needle 330 will be composed of an elastic material, typically an elastic or super elastic metal, typically being nitinol or other super elastic metal. Alternatively, the needle 330 could be formed from a non-elastically deformable or malleable metal which is shaped as it passes through a deflection path. The use of non-elastically deformable metals, however, is less preferred since such metals will generally not retain their straightened configuration after they pass through the deflection path.

The bellows structure 344 may be made by depositing by parylene or another conformal polymer layer onto a mandrel and then dissolving the mandrel from within the polymer shell structure. Alternatively, the bellows 344 could be made from an elastomeric material to form a balloon structure. In a still further alternative, a spring structure can be utilized in, on, or over the bellows in order to drive the bellows to a closed position in the absence of pressurized hydraulic fluid therein.

After the therapeutic material is delivered through the needle 330, as shown in FIG. 8, the needle is retracted and the catheter either repositioned for further agent delivery or withdrawn. In some embodiments, the needle will be retracted simply by aspirating the hydraulic fluid from the bellows 344. In other embodiments, needle retraction may be assisted by a return spring, e.g., locked between a distal face of the piston 338 and a proximal wall of the distal tip 352 (not shown) and/or by a pull wire attached to the piston and running through lumen 341.

Figure 9A:
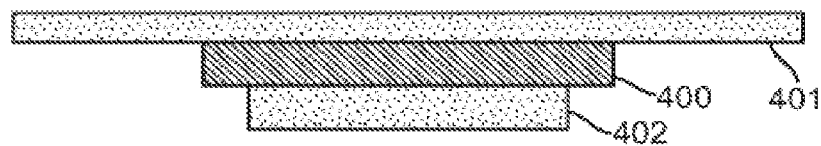
FIGS. 9A-9E are cross-sectional views of an exemplary fabrication process employed to create a free-standing low-modulus patch within a higher modulus anchor, framework or substrate.

FIGS. 9A-9E illustrate an exemplary process for fabricating a dual modulus balloon structure or anchored membrane structure in accordance with the principles of the present invention. The first step of the fabrication process is seen in FIG. 9A, in which a low modulus "patch", or membrane, material 400 is layered between removable (e.g. dissolvable) substrates 401 and 402. The substrate 401 covers one entire face of the patch 400, while the substrate 402 covers only a portion of the opposite face, leaving an exposed edge or border region about the periphery.

Figure 9B:
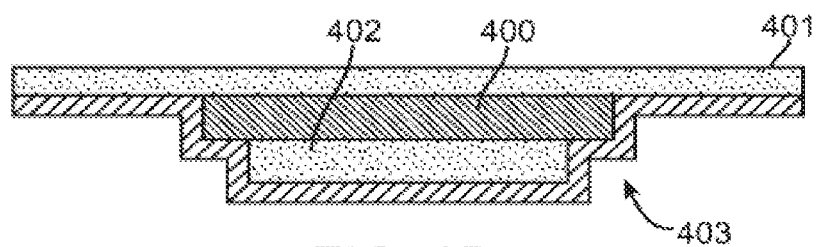

In FIG. 9B, a layer of a "flexible but relatively non-distensible" material 403 is deposited onto one side of the sandwich structure from FIG. 9A to provide a frame to which the low-modulus patch is attached. This material may be, for example, parylene N, C, or D, though it can be one of many other polymers or metals. When the flexible but relatively non-distensible material is parylene and the patch material is a silicone or siloxane polymer, a chemomechanical bond is formed between the layers, creating a strong and leak-free joint between the two materials. The joint formed between the two materials usually has a peel strength or interfacial strength of at least 0.05 N/mm$^2$, typically at least 0.1 N/mm$^2$, and often at least 0.2 N/mm$^2$.

Figure 9C:
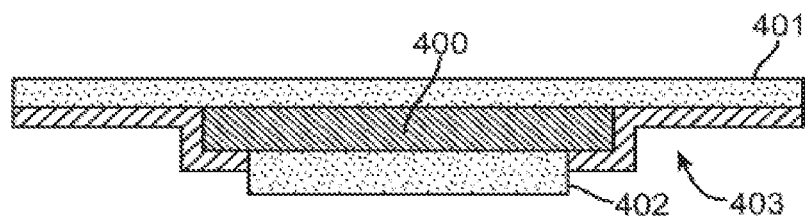
Figure 9D:
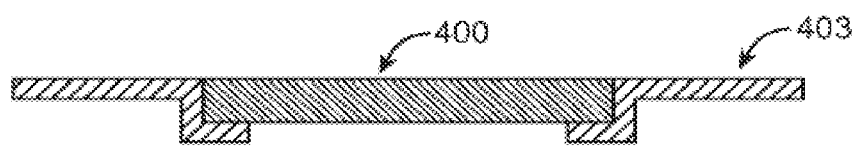

In FIG. 9C, the "flexible but relatively non-distensible" frame or anchor material 403 has been trimmed or etched to expose the substrate material 402 so that it can be removed. Materials 401 and 402 may be dissolvable polymers that can be removed by one of many chemical solvents. In FIG. 9D, the materials 401 and 402 have been removed by dissolution, leaving materials 400 and 403 joined edge-to-edge to form the low modulus, or elastomeric, patch 400 within a frame of generally flexible but relatively non-distensible material 403.

Figure 9E:
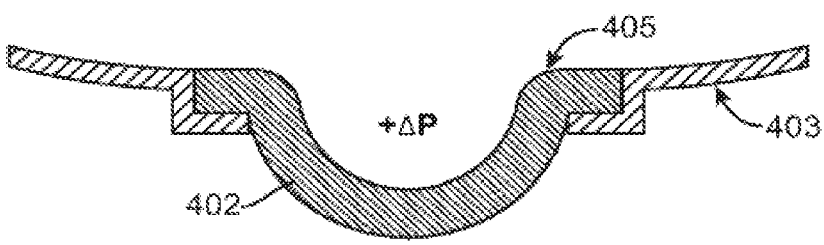

As shown in FIG. 9E, when positive pressure +ΔP is applied to one side 405 of the structure, the non-distensible frame 403 deforms only slightly, while the elastomeric patch 400 deforms much more. The low modulus material may have a material modulus which is always lower than that of the high modulus material and is typically in the range from 0.1 to 1,000 MPa, more typically in the range from 1 to 250 MPa. The high modulus material may have a material modulus in the range from 1 to 50,000 MPa, more typically in the range from 10 to 10,000 MPa. The material thicknesses may range in both cases from approximately 1 micron to several millimeters, depending on the ultimate size of the intended product. For the treatment of most body lumens, the thicknesses of both material layers 402 and 403 are in the range from 10 microns to 2 mm.

Figure 10A:
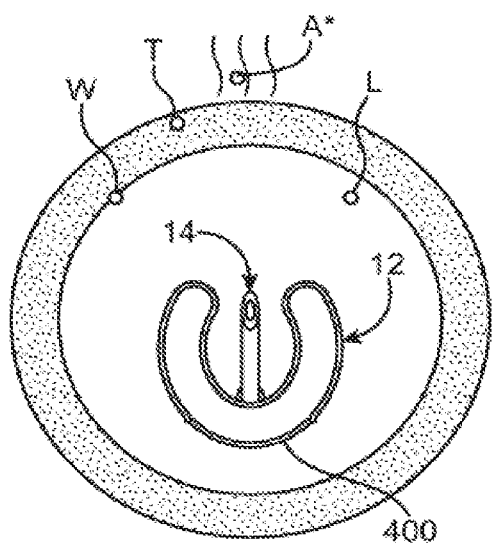
FIGS. 10A-10D are cross-sectional views of the inflation process of an intraluminal injection catheter useful in the methods of the present invention.

Referring to FIGS. 10A-10D, the elastomeric patch of FIGS. 9A-9D is integrated into the intraluminal catheter of FIG. 1-5. In FIG. 10A-D, the progressive pressurization of such a structure is displayed in order of increasing pressure. In FIG. 10A, the balloon is placed within a body lumen L. The lumen wall W divides the lumen from periluminal tissue T, or adventitia A*, depending on the anatomy of the particular lumen. The pressure is neutral, and the non-distensible structure forms a U-shaped involuted balloon 12 similar to that in FIG. 1 in which a needle 14 is sheathed. While a needle is displayed in this diagram, other working elements including cutting blades, laser or fiber optic tips, radiofrequency transmitters, or other structures could be substituted for the needle. For all such structures, however, the elastomeric patch 400 will usually be disposed on the opposite side of the involuted balloon 12 from the needle 14.

Figure 10B:
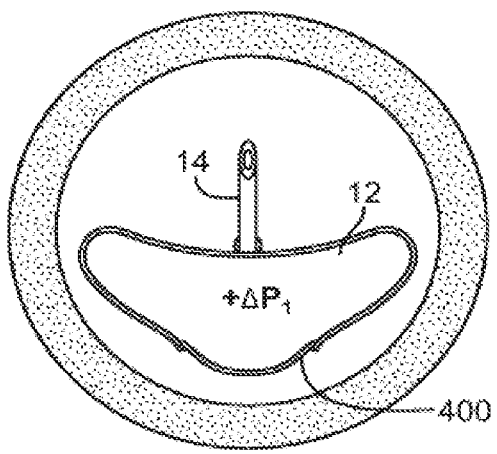
Figure 10C:
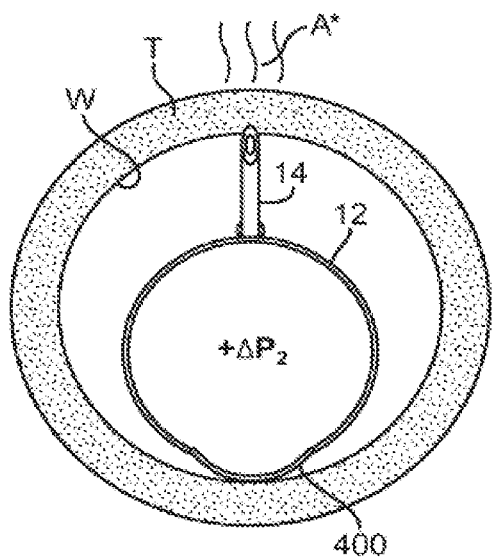
Figure 10D:
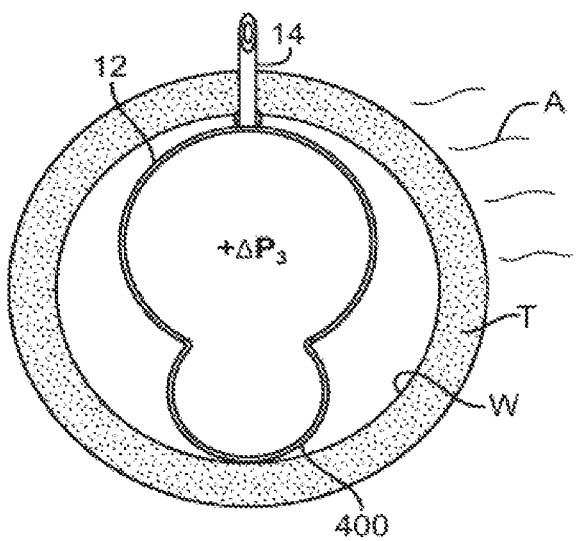

Actuation of the balloon 12 occurs with positive pressurization. In FIG. 10B, pressure ($+\Delta P_1$) is added, which begins to deform the flexible but relatively non-distensible structure, causing the balloon involution to begin its reversal toward the lower energy state of a round pressure vessel. At higher pressure $+\Delta P_2$ in FIG. 10C, the flexible but relatively non-distensible balloon material has reached its rounded shape and the elastomeric patch has begun to stretch. Finally, in FIG. 10D at still higher pressure $+\Delta P_3$, the elastomeric patch has stretched out to accommodate the full lumen diameter, providing an opposing force to the needle tip and sliding the needle through the lumen wall and into the adventitia. Typical dimensions for the body lumens contemplated in this figure are between 0.1 mm and 50 mm, more often between 0.5 mm and 20 mm, and most often between 1 mm and 10 mm. The thickness of the tissue between the lumen and adventitia is typically between 0.001 mm and 5 mm, more often between 0.01 mm and 2 mm and most often between 0.05 mm and 1 mm. The pressure $+\Delta P$ useful to cause actuation of the balloon is typically in the range from 0.1 atmospheres to 20 atmospheres, more typically in the range from 0.5 to 20 atmospheres, and often in the range from 1 to 10 atmospheres.

Figure 11A:
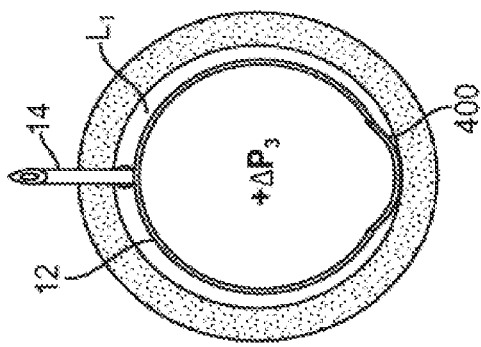
FIGS. 11A-11C are cross-sectional views of the inflated intraluminal injection catheter useful in the methods of the present invention, illustrating the ability to treat multiple lumen diameters.
Figure 11B:
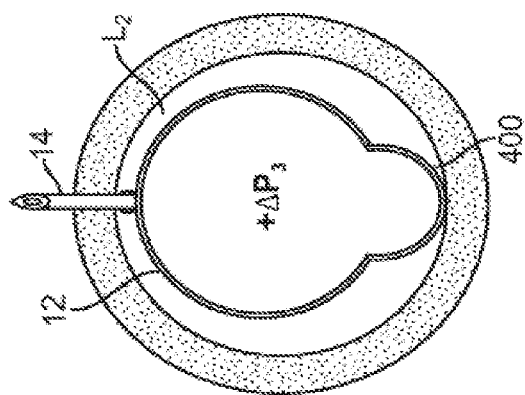
Figure 11C:
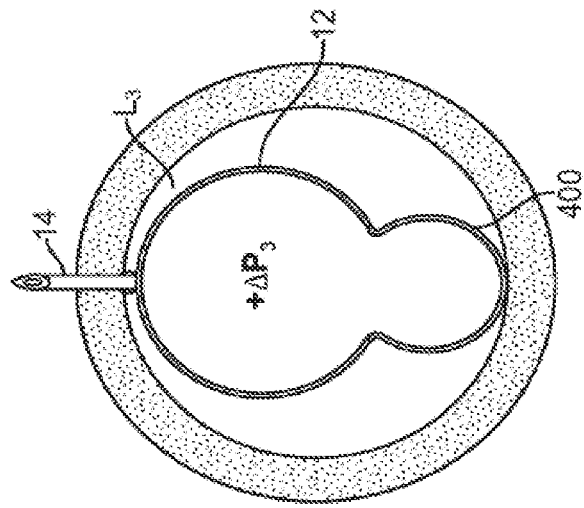

As illustrated in FIGS. 11A-11C, the dual modulus structure formed herein provides for low-pressure (i.e., below pressures that may damage body tissues) actuation of an intraluminal medical device to place working elements such as needles in contact with or through lumen walls. By inflation of a constant pressure, and the elastomeric material will conform to the lumen diameter to provide full apposition. Dual modulus balloon 12 is inflated to a pressure $+\Delta P_3$ in three different lumen diameters in FIGS. 11A, 11B, and 11C. for the progressively larger inflation of patch 400 provides optimal apposition of the needle through the vessel wall regardless of diameter. Thus, a variable diameter system is created in which the same catheter may be employed in lumens throughout the body that are within a range of diameters. This is useful because most medical products are limited to very tight constraints (typically within 0.5 mm) in which lumens they may be used. A system as described in this invention may accommodate several millimeters of variability in the luminal diameters for which they are useful.

Figure 12:
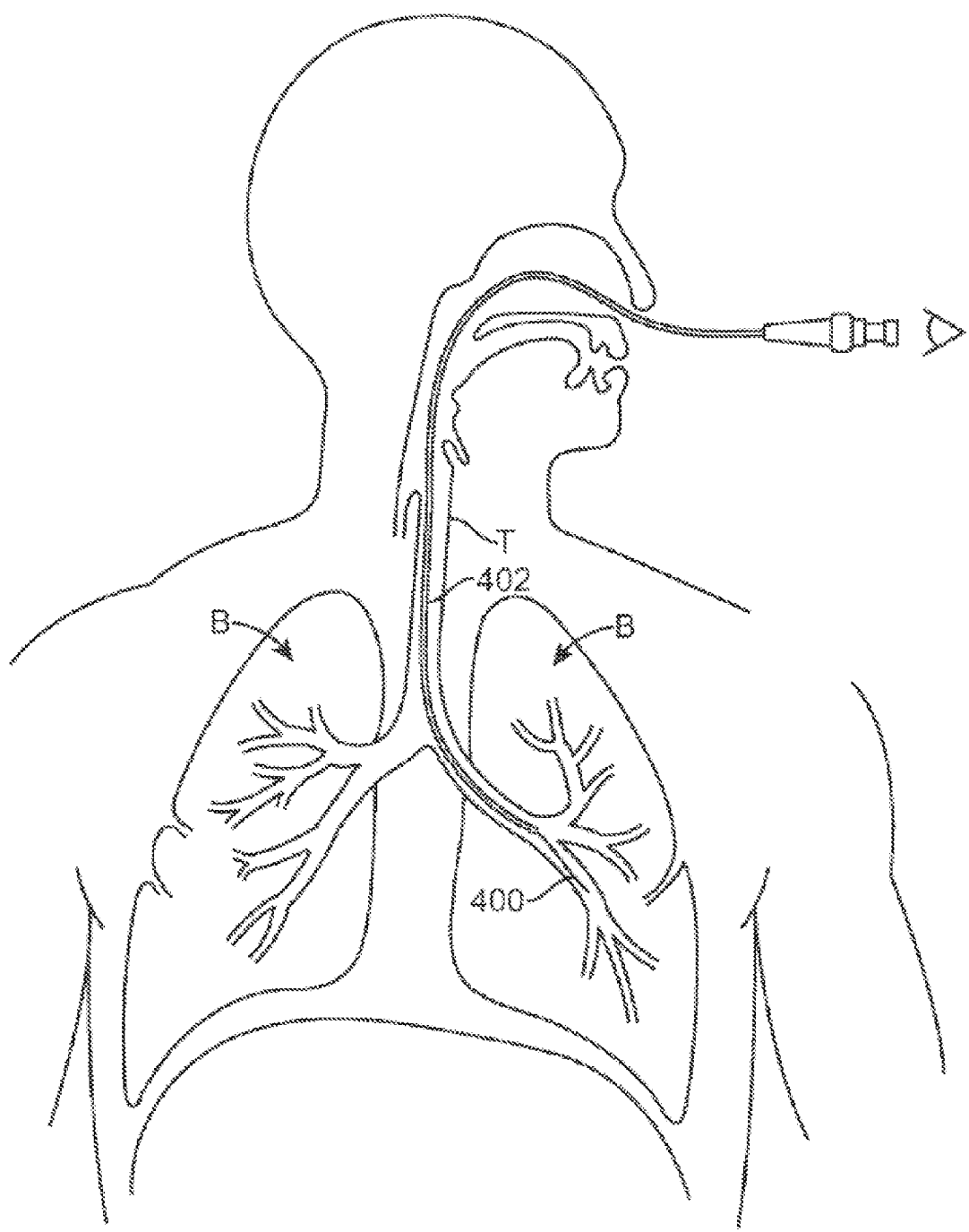
FIG. 12 is a diagram of representative conduits of the human respiratory system, including the bronchi B and trachea T, around which agents may be delivered according to the present invention.

Referring now to FIG. 12, body lumens, conduits, vessels, and cavitary organs that may be treated in accordance with the present invention are present in the respiratory system. A catheter 400 may be introduced to an area of therapeutic interest as described above. At that position, a needle is deployed through the wall of the conduit and medication is delivered. Of particular interest to this invention, medication may be deployed to reduce hyperconstrictive smooth muscle in the lungs, for example in asthmatic patients or in patients who have had a bronchial carcinoma debulked, where the catheter is typically delivered through a bronchoscope 402 (FIG. 12). Also, anti-cancer therapeutic agents may be delivered into tumors that lie near or around the conduit through which the catheter may be introduced and deployed (i.e., in lung). Anti-cancer therapeutic agents may be delivered to tumors or tumor sites in the bronchus to debulk the tumors or prevent recurrence of the tumors at the tumor sites. A variety of bronchial tumors may be treated, for example, a debridable tumor of bronchial tissue in the airway, a lobar airway stenosis for which mechanical tumor debridement is not feasible, and an extrinsic airway stenosis for which mechanical tumor debridement is not feasible (because mechanical debridement would likely destroy the airway).

Tracheomalacia, Bronchomalacia, Tracheobronchomalacia, Excessive Dynamic Airway Collapse The methods and systems described herein may also be applied to treat tracheomalacia, bronchomalacia, tracheobronchomalacia, or excessive dynamic airway collapse by maintaining patency in the tranchea or bronchus of a patient. Referring back to FIGS. 10A-10D and 11A-11C, the balloon 12 may be placed in the airway of the trachea or bronchus of the patient. The balloon 12 may then be expanded to position an aperture of the needle 14 beyond the periluminal tissue T and at the adventitia A. In many embodiments, the needle is configured to have a length so that the aperture is positioned at the media of the trachea or bronchus, which is between the adventitia and the lamina. Through the needle 12, a polymer precursor may be injected into the media. The polymer precursor may form a plume which migrates longitudinally and circumferentially through the media. The polymer precursor may then polymerize or solidify to form a solid section of artificial or prosthetic cartilage. This artificial or prosthetic cartilage may provide structural support to the trachea or bronchus, thereby threating the malacia. Similar methods and systems to treat malacia in other bodily lumens are also contemplated.

Aspects of the present disclosure may provide methods of maintaining patency in a trachea or a bronchus of a patient. An amount of a polymer precursor may be delivered to tissue in the trachea or bronchus. For example, 0.1 mL to 3 mL of the polymer precursor may be provided. In other examples, between 0.5 and 1 mL may be provided in each injection location. The polymer precursor at least partially solidifies in the tissue to provide support for the trachea or bronchus to maintain patency in the trachea or bronchus. Partial solidification may take the form of a gel or a hydrogel, in which case the material maintains some flexibility and lubricity, but generally provides a scaffolding to hold the airway open. The delivery may comprise injecting the amount of the polymer precursor into one or more of a wall, submucosa, lamina, media, or adventitia of the trachea or bronchus. The polymer precursor may at least partially solidify into a support member for the trachea or bronchus, thereby serving as artificial bronchial or tracheal cartilage. In many cases, the polymer precursor polymerizes to fully solidify.

The delivered amount of the polymer precursor may form a plume (e.g., a spread out volume or shape resembling a feather) that migrates circumferentially and/or longitudinally from a delivery site before at least partially solidifying.

In some embodiments, the delivery of the polymer precursor may comprise delivering an amount of a first polymeric precursor and an amount of a second polymeric precursor to the tissue. The first and second polymer precursor may react with one another to at least partially solidify. The amounts of the first and second crosslinking agents may be delivered sequentially. The amounts of the first and second crosslinking agents may react with one another to form a crosslinked polymer such as a hydrogel.

In some embodiments, an amount of an initiator may be delivered to the tissue. The initiator may cause polymerization of the polymer precursor in the tissue. For example, the initiator may facilitate or catalyze polymerization of the precursor into a hydrogel. The initiator may cause chemical activation of the polymerization for instance. For example, a two part polymeric material may be provided, such as silicone or a hydrogel, in which the first part initiates crosslinking only upon the addition of the second component of the mixture. In some cases, the second component may be a chemical catalyst and inherent part of the two part mixture. In other cases, the second component may only provide a condition in which polymerization of the first material takes place, such as a pH buffer.

In some embodiments, the delivered polymer precursor is exposed to an environmental stimulus. The environmental stimulus may cause polymerization of the polymer precursor in the tissue. The environmental stimulus may comprise one or more of light (e.g., luminosity decreases or increases, exposure to specific wavelengths of light such as UV, etc.), temperature (e.g., increases or decreases), pH (e.g., increases or decreases), ionic strength, electrical charge, or a hydrated environment, for example. For example, the environmental stimulus may facilitate or catalyze polymerization of the precursor into a hydrogel. The precursor may comprise, for example, a thermoreversible hydrogel such as that formed by amorphous N-substituted acrylamides in water, which may undergo reversible gelation when heated or cooled about certain temperatures. In an exemplary embodiment of temperature-based gelation, a two-part polyurethane is provided which flows at low temperature but becomes stable and cross links at body temperature. The polyurethane may be a shape memory polyurethane or a standard polyurethane. In an exemplary embodiment of a pH-based gelation, a self-assembling hydrogel such as Pura-Matrix™ is provided. Puramatrix material can be injected while liquid, and when it encounters physiologic pH in tissues, it assembles into polymeric chains, effectively forming a mesh of material in which water is trapped, thus, it is a hydrogel. Finally, UV-cure materials such as biocompatible UV-cure poly-methyl methacrylate may be injected in liquid form and then activated with UV light to cause cure of the material into a stiff, structural material.

In some embodiments, the polymer precursor comprises dehydrated hydrogel. The dehydrated hydrogel may rehydrate in the tissue to at least partially solidify.

The hydrogels and hydrogel precursors may comprise natural polymers such as glycosminoglycans (such as dermatan sulfate, hyaluronic acid, chondroitin sulfates, chitin, heparin, keratan sulfate, keratosulate, and the like), polysaccharides (such as carboxymethyl cellulose or oxidized regenerated cellulose, natural gum, agar, agrose, sodium alginate, carrageenan, fucoidan, furcellaran, laminaran, hypnea, eucheuma, gum arabic, gum ghatti, gum karaya, gum tragacanth, locust beam gum, arbinoglactan, pectin, amylopectin, gelatin, hydrophilic colloids such as carboxymethyl cellulose gum or alginate gum cross-linked with a polyol such as propylene glycol, and the like), proteins (such as albumin), etc. The natural polymers may combine to form a hydrogel. A water-soluble polymer such as polyvinyl pyrrolidone may crosslink with albumin derivatives, for example. The natural polymers may be modified synthetically from a naterual soluble state to a partially soluble or water swellable or hydrogel state. Synthetic polymeric hydrogels may be used as well. Examples may include poly(ethylene glycol), methoxypoly(ethylene glycol) monomethacrylate, hydrogels of poly(vinyl pyroolidone) and methacrylate, poly(hydroxyalkyl methacrylate), poly(electrolyte complexes), poly(vinylacetate) cross-linked with hydrolysable bonds, and water-swellable N-vinyl lactams, to name a few. Other hydrogels, hydrogel precursors, and catalysts or initiators are described in U.S. Pat. No. 8,105,622 to Sawhney, which is incorporated herein by reference.

To deliver the amount of polymer precursor, a needle may be positioned through a wall of the bronchus or the trachea so that an aperture of the needle is positioned at or beyond the lamina of the trachea or bronchus. The needle may comprise a 25 to 45 gauge needle. In some embodiments, the aperture of the needle is positioned at the media of the trachea or bronchus so that the amount of the polymer precursor is delivered therein.

It may be further confirmed that the polymer precursor is penetrating the tissue by imaging either the polymer precursor mixed with a diagnostic agent or by delivery of a diagnostic agent prior to the delivery of the polymer precursor.

The method may further comprise steps of advancing a catheter into an airway of the trachea or bronchus and positioning the catheter adjacent a target region of the tracheal or bronchial wall and adventitia before delivery of the polymer precursor. To deliver the amount of the polymeric precursor, an expandable element disposed on a distal end of the positioned catheter may be expanded to cause a needle disposed on the expandable element to puncture the target region of the wall, submucosa, media, or adventitia of the trachea or bronchus before delivery of the polymeric precursor. The expandable element may comprise an inflatable balloon, and the expandable element may be expanded by inflation of the inflatable balloon. For example, the inflatable balloon may be inflated with 2 atmospheres of pressure without damaging the bronchus. The inflatable balloon may be inflated with air, saline, or a buffer.

In some embodiments, rather than the delivery of polymeric filler material or biologic material such as collagen, a sclerosing or fibrosing material may be delivered to the airway wall in order to cause the tissue to scar or fibrose, stiffening in response to the irritant medium. In these cases as with the delivery of polymeric materials described above, a stent may be temporarily placed as a shape cast to set the desired shape of the airway while polymers set or while biological irritants lead to fibrosis or stiffening of the airway wall.

Experimental Studies

Data from pre-clinical studies suggests that injecting paclitaxel into the bronchial adventitia using the balloon mounted injection needle described herein at a 0.5 mg/mL dose is safe. These studies demonstrate the ability to achieve high local concentrations of the therapeutic agent within the wall of the bronchus with no observable systemic or local parechymal toxicity.

Paclitaxel is a commercially available generic therapeutic agent with antitumor activity discovered in the 1970s. It is a clear, colorless, slightly viscous liquid, and the formulation of each one mL of solution contains 6 mg of active pharmaceutical ingredient paclitaxel. Paclitaxel is approved worldwide for treatment of non-small cell lung cancer, ovarian, and breast carcinoma, and AIDS-related Kaposi's sarcoma and has been extensively studied pre-clinically and clinically as a part of obtaining the requisite regulatory approvals. Typically, it is systemically administered via intravenous infusion over several hours at doses ranging between 135 and 175 mg/m$^2$ depending on the infusion duration. Adverse drug reactions associated with the systemic administration are well known.

Generic and proprietary paclitaxel formulations have been extensively studied not just for the approved indications, but also for other indications. Paclitaxel is an antimicrotubule agent that promotes the assembly of microtubules from tubulin dimers and stabilizes microtubules by preventing depolymerization. This stability results in the inhibition of the normal dynamic reorganization of the microtubule network that is essential for vital interphase and mitotic cellular functions. In addition, paclitaxel induces abnormal arrays or "bundles" of microtubules throughout the cell cycle and multiple asters of microtubules during mitosis. As a result, paclitaxel inhibits normal cell proliferation.

Paclitaxel can be used in the treatment of different solid tumors. Paclitaxel alone (generic and proprietary formulations) is used as a first and second line treatment against ovarian, breast, lung and other types of carcinoma. It is also used in combination with carboplatin and other agents.

Systemic administration of paclitaxel can lead to toxicities to normal tissues. Paclitaxel is a chemotherapeutic agent, but as such it could cause toxic effects on peripheral nerves with different severities. Peripheral neuropathy could be dose-limiting side effect.

Paclitaxel has been extensively studied as part of obtaining marketing approval in the USA (NDA 020262) and world-wide and it is being currently investigated for other indications and in combination with newly discovered agents (NCT00021060). As of June 2013, there are over 1900 studies listed on www.clinicaltrials.gov involving paclitaxel, of which 396 are investigating paclitaxel in lung cancer, and of them 71 are currently recruiting patients. Thirty two (32) of the currently recruiting studies are enrolling patients with stage IV lung cancer. This demonstrates a clinical need for paclitaxel as a therapeutic agent for lung cancer. At the same time, there is a vast safety database for paclitaxel that has been accumulated over the years.

In the pre-clinical studies performed, paclitaxel was delivered using the Blowfish Transbronchial Micro-Infusion Catheter available from Mercator Medsystems of San Leandro, Calif., which is commercially available and intended to deliver therapeutic and diagnostic agents that are indicated or labeled for airway, tracheal, or bronchial delivery into selected and sub-selected regions of the airway tree.

Generic Paclixtaxel (Taxol) Studies

A GLP study with 10 pigs and two paclitaxel concentrations was conducted. Injections of saline (placebo) or 0.4 and 1.5 mg/mL paclitaxel (PTX) to the bronchial adventitia of Yorkshire pigs using a Mercator Blowfish Transbronchial Micro-Infusion Catheter were well-tolerated by the animals under the conditions of this study. Other than a transient reaction to PTX or excipient (Cremophor EL) for a single animal administered 1.5 mg/mL PTX infusions, there were no other infusion or PTX related abnormalities in the clinical observations, body weights, and clinical pathology results. Microscopic evaluation after 28 days was associated with favorable local tissue responses that were comparable between the saline control, low doses (0.5 mg/mL) and high does (1.5 mg/mL) PTX groups. Injury was absent to negligible, and comparable between Treated and Control groups. Epithelial loss was negligible across groups, and fibrin/luminal hemorrhage/thrombus absent to negligible. Inflammation associated with treatment was also absent to negligible, and the minimal lymphocytes present were considered part of normal BALT. One individual female animal from the Placebo Control group exhibited multifocal pneumonia and mild bronchial inflammation that was unrelated to PTX, and may have been caused by bronchoscopic procedure alone or due to an infectious inhalant or non-infectious aspiration etiology.

Figure 13:
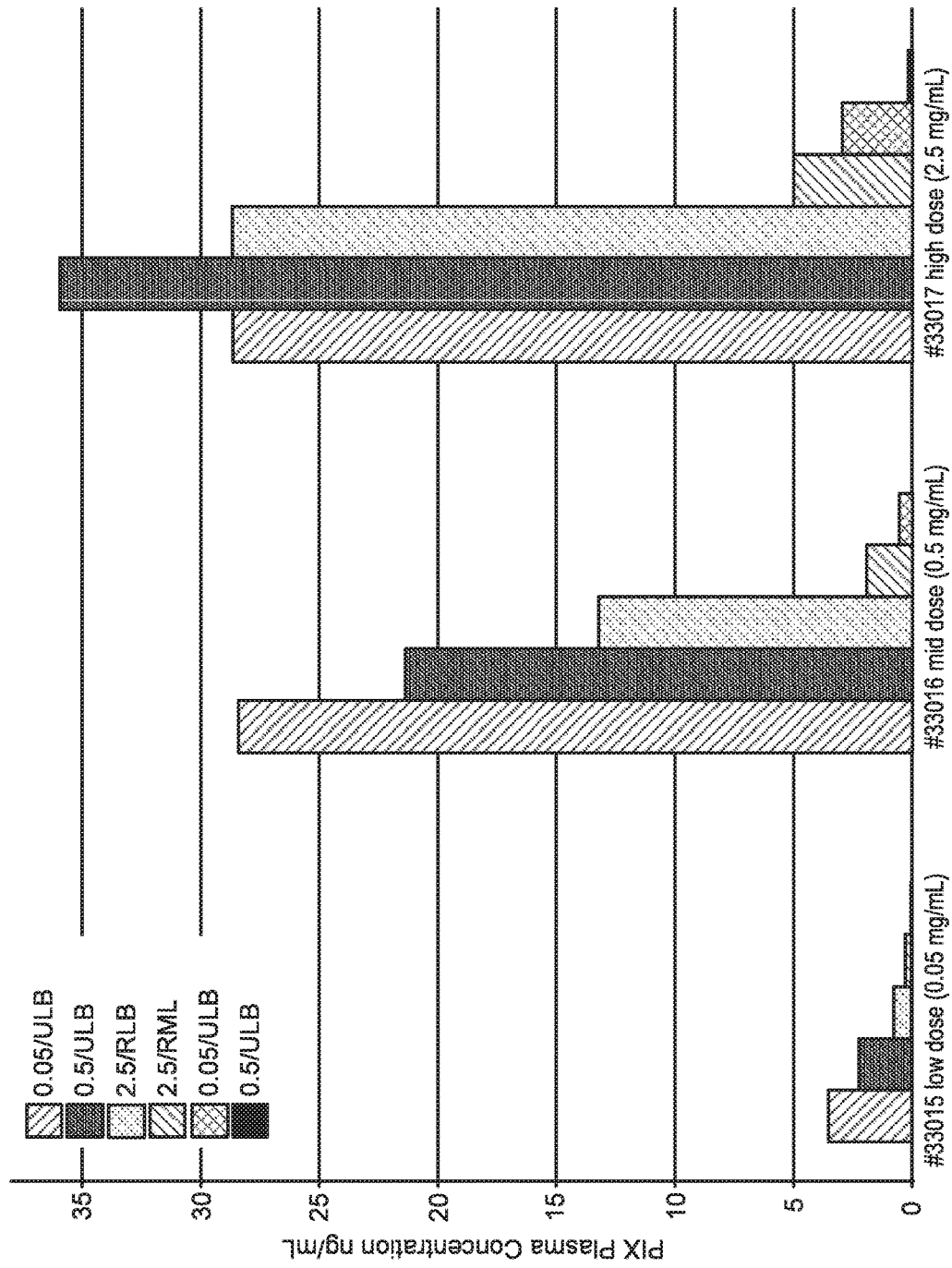
FIG. 13A is a chart of paclitaxel plasma concentrations over 7-days for various local dosages of paclitaxel in a porcine study.
FIG. 13B is a graph of paclitaxel plasma concentrations (AUC Curves) over 7-days for various local dosages of paclitaxel in a porcine study.
Figure 13B:
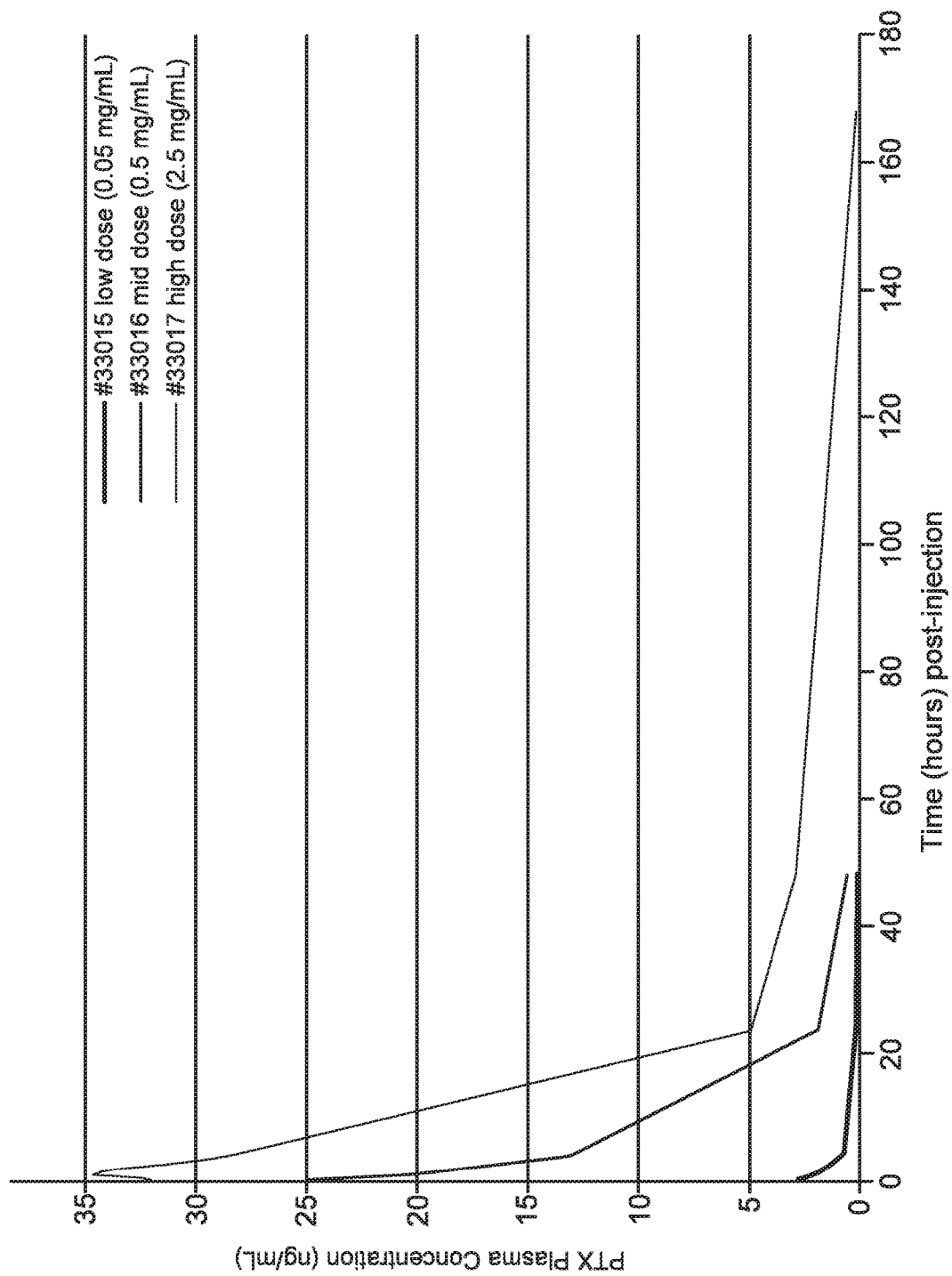

As shown in FIGS. 13A and 13B, PTX was not present in the plasma of control animals, but was measured in plasma samples of both drug groups out to 120 hours (5 days). No PTX was detected at 28 days post infusion in any animal. The $AUC_{(0-5d)}$ was calculated to be 122±15 ng*h/mL for the 0.5 mg group (with an average total dose of 5.2±0.3 mg across 10.3±0.6 infusions) and 320±61 ng*h/mL for the 1.5 mg group (with a total dose of 15 mg in each animal). These $AUC_{(0-5d)}$ levels meet the acceptance criterion established by the paclitaxel package insert, which describes an AUC (0-∞) of 6,300 ng*h/mL for a 135 mg/m$^2$ dose administered over 24 hours.

Figure 14:
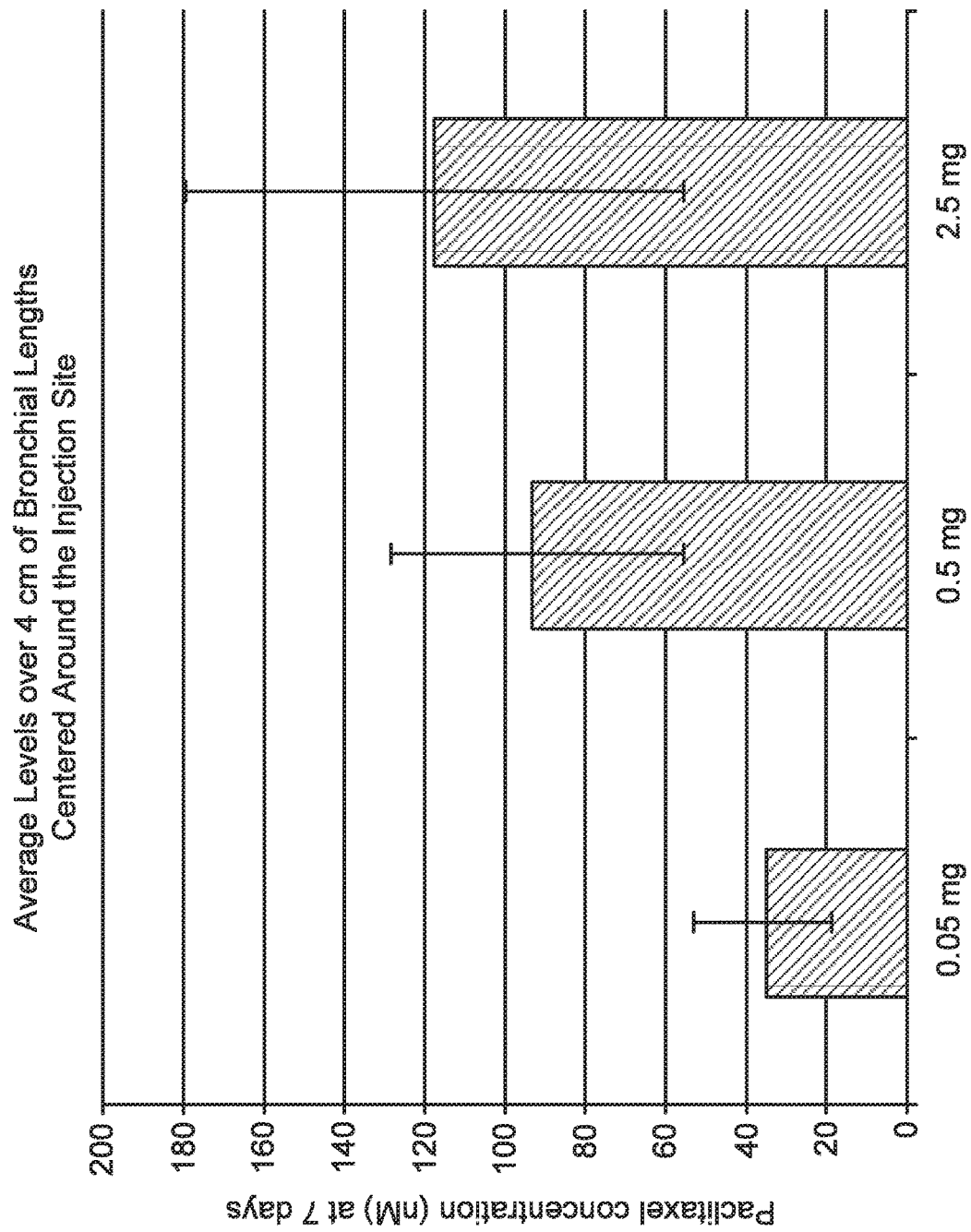
FIG. 14 is a graph of average paclitaxel concentration at 7 days over 4 cm of bronchial tissue centered around an injection site (2 cm distal and 2 cm proximal).
Figure 15:
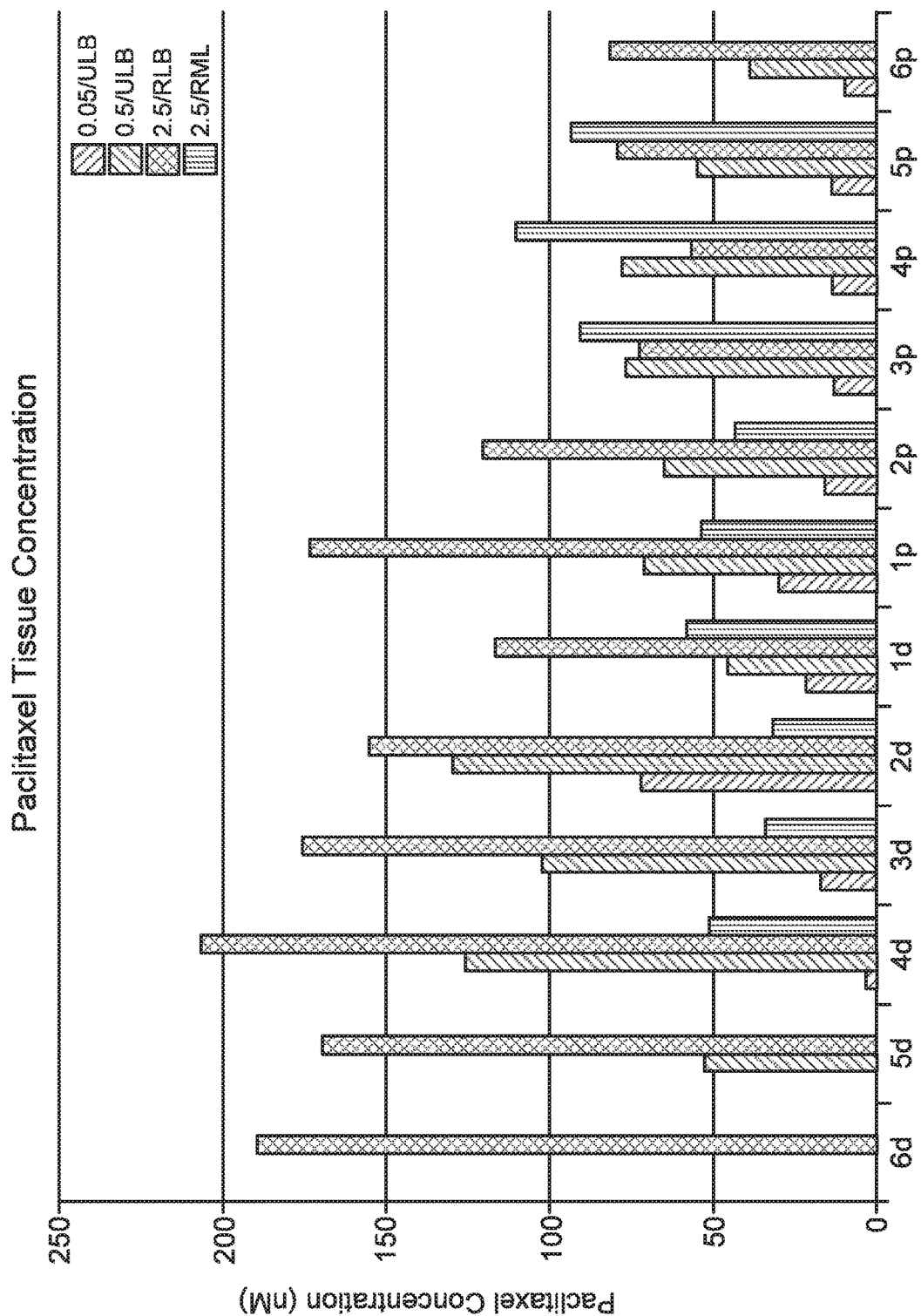
FIG. 15 is a graph of paclitaxel plasma levels in individual bronchial segments up to 6 cm from the injection Site (between 1d=1 cm distal from the injection site and 1p=1 cm proximal).

Paclitaxel Tissue Concentrations: Bronchial tissue was collected for tissue PTX analysis. FIG. 14 shows the average paclitaxel concentration (nM) at 7 days over 4 cm of bronchial tissue centered around the injection site (2 cm distal and 2 cm proximal). Average paclitaxel concentrations in the first two distal and first two proximal segments in each dose group (low, mid and high) were 35±15 nM (range from 14.7 nM to 50.4 nM), 86±33 nM (ranging from 26.7 nM to 122.1 nM) and 94±67 nM (ranging from 47.1 nM to 141.4 nM), respectively. Since the drug was present in these concentrations at 7 days, these drug tissue levels are above the 10-30 nM values reported in the literature as effective if present for 96 hours in suppressing cancer cell lines such as H358 an H460 [Zou et al., 2004]. In each dose group, there was one injection site for which all collected distal and proximal samples were analyzed (FIG. 15). For segments in FIG. 15 in which no column is present, it is not a zero measurement, but a lack of tissue sample corresponding to the omitted columns.

From a review of the tissue results in conjunction with the plasma concentration data, it can be concluded that paclitaxel was present in bronchial tissue of the 0.5 and the 1.5 mg/mL paclitaxel groups even after 28 days, while at the same time the local tissue reaction was mild to negligible in all groups.

Histopathology and Drug Tissue Concentration One Week after Paclitaxel Delivery to Porcine Bronchial Adventitia In Vivo:

After 7 days in porcine model, treatment of bronchial wall using the Mercator Blowfish Transbronchial Micro-Infusion Catheter for paclitaxel delivery was associated with evidence of a lymphocytic response and mild inflammation at doses of 0.05 mg per injections site and 0.5 mg per injection site however these doses were not associated with evidence of damage. Specifically there was no evidence of luminal thrombus bronchial injury and minimal epithelial loss.

At the highest dose tested (2.5 mg/mL, i.e. 5 mg per injection site), there was multifocal marked subacute necrosis of bronchial cartilage, peribronchial tissue and pulmonary parenchyma, with moderate associated inflammation. Mean bronchial injury in this group was moderate (i.e. lacerated smooth muscle), while luminal thrombus and epithelial loss were overall minimal.

Plasma paclitaxel concentrations decreased over time. In the low (0.05 mg/site, i.e. 0.65 mg total paclitaxel injected) and medium (0.5 mg/site, i.e. 6.5 mg total paclitaxel injected) dose pigs they were below the method's Limit of Quantitation (LOQ=0.03 ng/mL) at 7 days. In the high dose animal (5 mg paclitaxel per site and total of 25 mg paclitaxel injected), even at 7 days, the paclitaxel plasma concentration was at detectible levels (at 0.124 ng/mL).

Paclitaxel plasma concentration area under the curve (AUC): $AUC_{last}$ for the low dose (0.65 mg of total paclitaxel) and medium dose (6.5 mg of total paclitaxel) was 18.46 ng*h/mL and 255.5 ng*h/mL, respectively and $AUC_{last}$ for the high dose pig was 740.40 ng*h/mL. These values are lower than what has been reported for IV administered paclitaxel in the FDA approved Package Insert for Taxol (NDA 020262): $AUC_{(0-\infty)}$ between 6,300 and 15,007 ng*h/mL. As the local dosing resulted in lower systemic exposure than currently approved doses, no new systemic toxic effects are anticipated.

It is noted that concentrations of around 20 nM of paclitaxel were found to be effective in suppressing cancer cell lines such as H358 and H460 according to various studies in the literature. Average paclitaxel concentrations in the first two distal and first two proximal segments in each dose group (low, mid and high) were 35±15 nM, 86±33 nM and 94±67 nM, respectively. Since the drug was present in these concentrations at 7 days, these drug tissue levels are likely above the 10-30 nM values reported in the literature as effective if present for 96 hours in suppressing cancer cell lines such as H358 an H460.

The data above indicate that it was safe to deliver paclitaxel at 0.05 and 0.5 mg/mL dose levels using the Blowfish Catheter. Injecting 2 mL of paclitaxel at 2.5 mg/mL, i.e. 5 mg paclitaxel per site was found to cause local adverse reactions that could be considered dose-limiting toxicities. Plasma paclitaxel levels drop below the LOQ of the method within 7 days for the low and mid dose but are sustained above LOQ for the high dose to 7 days. The tissue paclitaxel concentration data indicate that there is sufficient drug in the bronchial adventitia at cancer inhibiting levels, yet there were no observed systemic toxicities in any of the studied concentrations.

Abraxane® Studies

Studies using 0.5 mg/mL Abraxane® (a proprietary paclitaxel formulation) instead of Taxol, i.e. generic paclitaxel, formulated with Cremophor EL were conducted. These 1-, 7- and 20-day studies also indicated that injecting paclitaxel active ingredient into the bronchial wall was safe and resulted in chemotherapeutic concentrations at all timepoints analyzed. The local tissue reaction to the infusion of paclitaxel was negligible, and there were no injuries or epithelial loss in paclitaxel injected segments. Focal findings of inflammation and Hemorrhage/Fibrin/Thrombus were at worst mild on average. No injury or epithelial loss was found beyond 1 day in paclitaxel injected segments.

Study Conclusions

These studies demonstrate that: (1) Blowfish Catheter injection is safe; (2) paclitaxel injections into the bronchial wall at 1.5 mg/mL dose or less are safe; (3) tissue levels of paclitaxel are maintained at cancer-inhibiting levels to 7 days for generic paclitaxel and to 20 days for Abraxane®. Thus, Applicants believe paclitaxel is suitable for the treatment of non-small cell lung cancer by localized delivery in the airway wall with a proposed dose of 1.5 mg/mL, with a total of 1.5 mg/subject.

Studies with Filler Materials:

Studies have been performed to deliver bulking agents directly into the airway wall using a self-assembling hydrogel matrix, and separately, with a collagen filler material. In each case, cartilage content was removed from the airway of a sheep and the material was injected into the airway wall in an attempt to create a supportive scaffolding directly inside the airway wall. In each case, injections of 0.5 to 1.0 mL were made in several locations approximately 5 mm to 10 mm apart. On long term (30 day) follow-up, the subjects were found to not have produced a toxic response to the injected agent, and the airway was widely patent in each case rather than having collapsed due to the removal of the cartilage scaffold from the airway.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method of maintaining patency in a trachea or a bronchus of a patient, the method comprising:
    delivering an amount of a polymer precursor to a tissue in the trachea or the bronchus, wherein the delivered amount of the polymer precursor at least partially solidifies in the tissue to provide support for the trachea or the bronchus to maintain patency in the trachea or the bronchus, wherein delivering comprises injecting the amount of the polymer precursor into one or more of a wall, a submucosa, a lamina, a media, or an adventitia of the trachea or the bronchus, and wherein the delivered amount of the polymer precursor forms a plume that migrates one or more of circumferentially or longitudinally from a delivery site before at least partially solidifying.

2. The method of claim 1, wherein delivering an amount of the polymer precursor comprising delivering an amount of a first polymeric precursor and an amount of a second polymeric precursor to the tissue, wherein the first and second polymer precursor react with one another to at least partially solidify.

3. The method of claim 2, wherein the amounts of the first and second polymeric precursors are delivered sequentially.

4. The method of claim 2, wherein the amounts of the first and second polymeric precursors react with one another to form a crosslinked polymer.

5. The method of claim 4, wherein the crosslinked polymer comprises a hydrogel.

6. The method of claim 1, further comprising delivering an amount of an initiator to the tissue, wherein the initiator causes polymerization of the polymer precursor in the tissue.

7. The method of claim 1, further comprising exposing the delivered amount of the polymer precursor to an environmental stimulus, wherein the environmental stimulus causes polymerization of the delivered amount of the polymer precursor in the tissue.

8. The method of claim 7, wherein the environmental stimulus comprises one or more of light, temperature, pH, ionic strength, electrical charge, or a hydrated environment.

9. The method of claim 1, wherein the polymer precursor comprises a dehydrated hydrogel, wherein the dehydrated hydrogel rehydrates in the tissue to at least partially solidify.

10. The method of claim 1, wherein delivery comprises positioning a needle through the wall of the bronchus or the trachea so that an aperture of the needle is positioned at or beyond the lamina of the trachea or the bronchus.

11. The method of claim 10, wherein the needle comprises a 25 to 45 gauge needle.

12. The method of claim 10, wherein the aperture of the needle is positioned at the media of the trachea or the bronchus so that the amount of the polymer precursor is delivered therein.

13. The method of claim 1, further comprising confirming that the polymer precursor is penetrating the tissue by imaging either the polymer precursor mixed with a diagnostic agent or the diagnostic agent delivered prior to the delivery of the polymer precursor.

14. The method of claim 1, further comprising:
  advancing a catheter into an airway of the trachea or the bronchus; and
  positioning the catheter adjacent a target region of the tracheal or bronchial wall and adventitia before delivery of the amount of the polymer precursor.

15. The method of claim 14, wherein delivering the amount of the polymeric precursor further comprises:
  expanding an expandable element disposed on a distal end of the positioned catheter to cause a needle disposed on the expandable element to puncture the target region of the wall, the submucosa, the media, or the adventitia of the trachea or the bronchus before delivery of the amount of the polymeric precursor.

16. The method of claim 15, wherein the expandable element comprises an inflatable balloon, and expanding the expandable element comprises inflating the inflatable balloon.

17. The method of claim 16, wherein inflating the inflatable balloon comprises inflating the inflatable balloon with 2 atmospheres of pressure without damaging the bronchus.

18. The method of claim 16, wherein the inflatable balloon is inflated with air, saline, or a buffer.

19. The method of claim 1, wherein the delivered amount of the polymer precursor at least partially solidifies into a support member for the trachea or the bronchus.

20. The method of claim 1, wherein the patient has been diagnosed with tracheal malacia, bronchial malacia or excessive dynamic airway collapse.

\* \* \* \* \*